US006106834A

United States Patent [19]
Lazarovits et al.

[11] Patent Number: 6,106,834
[45] Date of Patent: *Aug. 22, 2000

[54] USE OF ANTI-CD45 LEUKOCYTE ANTIGEN ANTIBODIES FOR IMMUNOMODULATION

[75] Inventors: Andrew I. Lazarovits, London, Canada; Sibrand Poppema, Bunne, Netherlands

[73] Assignee: Research Corporation Technologies, Inc., Tucson, Ariz.

[*] Notice: This patent is subject to a terminal disclaimer.

[21] Appl. No.: 08/715,342

[22] Filed: Sep. 18, 1996

Related U.S. Application Data

[63] Continuation-in-part of application No. 08/423,843, Apr. 18, 1995, which is a continuation-in-part of application No. 08/071,009, Jun. 2, 1993, abandoned.

[51] Int. Cl.[7] .......................... A61K 39/395; C07K 16/28
[52] U.S. Cl. ..................................... 424/172.1; 424/173.1; 424/144.1; 424/130.1; 530/387.1; 530/388.7; 530/388.73; 530/388.75; 530/388.85; 530/389.6
[58] Field of Search .............................. 424/130.1, 172.1, 424/173.1, 144.1; 530/387.1, 388.7, 388.73, 388.75, 388.85, 389.6

[56] References Cited

U.S. PATENT DOCUMENTS

| | | | |
|---|---|---|---|
| 4,626,507 | 12/1986 | Trowbridge et al. | 435/240 |
| 5,100,899 | 3/1992 | Calne | 514/291 |
| 5,565,491 | 10/1996 | Schieven | 514/492 |

FOREIGN PATENT DOCUMENTS

| | | | |
|---|---|---|---|
| 0449769 | 10/1991 | European Pat. Off. | C07K 15/28 |
| 91/05568 | 5/1991 | WIPO | A61K 39/395 |
| 93/00431 | 1/1993 | WIPO | C12N 15/12 |
| WO95/14230 | 5/1995 | WIPO . | |
| WO96/32965 | 10/1996 | WIPO . | |

OTHER PUBLICATIONS

Sewer, Gen Eng News 14:10, 1994.
Nishikawa, M., et al., "Effects of Monoclonal Antibody against CD45RB on Peripheral Blood Mononuclear Cell Proliferation and on HLA–DR and Adhesion Molecule Expression on Thyrocytes of Patients with Autoimmune Thyroid Disease", *Thyroid*, vol. 5, No. 4, pp. 265–272, (1995).
Ozcay, N., et al., "Prevention of heart allograft rejection by monoclonal antibody to CD45RB", *Turk. J. Surg.*, vol. 11, No. 6, pp. 372–376, (1995) Abstract Only.
Streuli, M., et al., "Characterization of CD45 and CD45R Monoclonal Antibodies Using Transfected Mouse Cell Lines That express Individual Human Leukocyte Common Antigens", *J. Immunology.*, vol. 141, No. 11, 3910–3914, (Dec., 1988).
R. J. Benjamin, et al., "Induction of Tolerance by Monoclonal Antibody Therapy", *Nature*, 320, 449–451, (1986).
C. I. Bindon, et al., "Therapeutic Potential of Monoclonal Antibodies to the Leukocyte–Common Antigen", *Transplantation*, 40, 538–544, (1985).

M L Birkeland, et al., "Epitopes on CD45R (T200) Molecules Define Differentiation Antigens on Murine B and T Lymphocytes", *J. Mol. Cell. Immunol.*, 4, 71–85, (Nov., 1988).
Y. Brewer, et al., "Effect of Graft Perfusion with Two CD45 Monoclonal Antibodies on Incidence of Kidney Allograft Rejection", *Lancet*, 935–937, (Oct., 1989).
L. Chatenoud, et al., "Anti–CD3 Antibody Induces Long–Term Remission of Overt Autoimmunity in Nonobese Diabetic Mice", *Proc. Natl Acad. Sci. USA*, 91, 123–127, (Jan., 1994).
A. B. Cosimi, et al., "In Vivo Effects of Monoclonal Antibody to ICAM–1 (CD54) in Nonhuman Primates with Renal Allografts", *J. Immunol.*, 144, 4604–4612, (1990).
J. W. Fabre, et al., "Immunosuppressive Properties of Rabbit Antibodies Against a Major Glycoprotein Restricted to Rat Leukocyte Membranes", *Transplantation*, 30, 167–173, (Sep., 1980).
J. W. Fabre, et al., "Quantitative Serological Analysis ofa Rabbit Anti–Rat Lymphocyte Serum and Preliminary Bio-Chemical Characterization of the Major Antigen Recognized", *Transplantation*, 23, 349–359, (Apr., 1977).
J. L. Fahey, et al., "Status of Immune–Based Therapies in HIV Infection and Aids", *Clin. Exp. Immunol.*, 88, 1–5, (Jan., 1992).
G. Hale, et al., "Pilot Study of Campath–1, a Rat Monoclonal Antibody that Fixes Human Complement, as an Immunosuppressant in Organ Transplantation", *Transplantation*, 42, 308–311, (Sep., 1986).
W. J. Harris, et al., "Therapeutic Antibodies—The Coming of Age", *Tibtech, vol. II*, Meeting Report, 42–44, (Feb., 1993).
R. Hasan, et al., "Evidence That Long–Term Survival of Concordant Xenografts is Achieved by Inhibition of Anti-species Antibody Production", *Transplantation*, 54, 408–413, (Sep., 1992).
C. E. Haug, et al., "A Phase I Trial of Immunosuppression With Anti–ICAM–1 (CD54) mAb in Renal Allograft Recipients", *Transplantation*, 55, 766–773, (Apr., 1993).
M. Isobe, et al., "Specific Acceptance of Cardiac Allograft After treatment with Antibodies to ICAM–1 and LFA–1", *Science*, 255, 1125–1127, (Feb., 1992).
L. K. Jolliffe, "Humanized Antibodies: Enhancing Therapeutic Utility Through Antibody Engineering", *Intern. Rev. Immunol.*, 10, 241–250, (1993).
M. Jonker, et al., "The Influence of OKT8F Treatment on Allograft Survival in Rhesus Monkeys", *Transplantation*, 41, 431–435, (Apr., 1986).

(List continued on next page.)

*Primary Examiner*—Nancy A Johnson
*Attorney, Agent, or Firm*—Schwegman, Lundberg, Woessner & Kluth, P.A.

[57] ABSTRACT

A method for the prevention or reversal of transplant rejection, or for therapy for autoimmune diseases, is provided comprising administering compounds such as monoclonal antibodies, that bind specifically to one or more preselected CD45R leukocyte antigens, including the CD45RB epitope.

19 Claims, 7 Drawing Sheets

OTHER PUBLICATIONS

R. L. Kirkman, et al., "A Randomized Prospective Trial of Anti–TAC Monoclonal Antibody in Human Renal Transplantation", *Transplantation*, 51, 107–113, (Jan., 1991).

R. L. Kirkman, et al., "The Effect of Anti–Interleukin–2–Receptor Monoclonal Antibody on Allograft Rejection", *Transplantation*, 40, 719–772, (Dec., 1985).

R. Lai, et al., "Tissue Distribution of Restricted Leukocyte Common Antigens–A Comprehensive Study with Protein–and Carbohydrate–Specific CD45R Antibodies", *Laboratory Investigation*, 64, See Table 2, 844–854, (Jun., 1991).

A. I. Lazarovits, et al., "A Monoclonal Antibody, 7G5 (CD7), Induces Modulation of Tp40 and Inhibits Proliferation in the Allogeneic and Autologous Mixed Lymphocyte Reactions", Transplant. Proc., 20, 1253–1257, (Dec., 1988).

A. I. Lazarovits, et al., "Human Mouse Chimeric CD7 Monoclonal Antibody (SDZCHH380) for the Prophylaxis of Kidney Transplant Rejection", *J. Immunol.*, 150, 5163–5174, (Jun., 1993).

A. I. Lazarovits, et al., "Inhibition of Alloreactivity in Vitro by Monoclonal Antibodies Directed Against Restricted Isoforms of the Leukocyte–Common Antigen (CD45)", *Transplantation*, 54, 724–729, (Oct., 1992).

A. I., Lazarovits, et al., "Prevention and Reversal of Renal Allograft Rejection by Antibody Against CD45RB", *Nature*, 380, 717–720, (Apr., 1996).

A. I. Lazarovits, "T Lymphocyte Activation and CD45/45R Antibodies (Mab)", *Tissue Antigen—Histocompatibility and Immunogenetics*, 33, Abstract, 275, (Feb., 1989).

W. J. Leonard, et al., "A Monoclonal Antibody that Appears to Recognize the Receptor for Human T–Cell Growth Factor; Partial Characterization of the Receptor", *Nature*, 300, 267–269, (1982).

P. W. Mathieson, et al., "Monoclonal–Antibody Therapy in Systemic Vasculitis", *N. Eng. J. Med.*, 323, 250–254, (Jul., 1990).

E. K. Nakakura, et al., "Potent And Effective Prolongation By Anti–LFA–1 Monoclonal Antibody Montherapy Of Non–Primarily Vascularized Heart Allograft Survival In Mice Without T Cell Depletion", *Transplantation*, 55, 412–417, (Feb., 1993).

M. R. Nicolls, et al., "Induction of Long–Term Specific Tolerance to Allografts in Rats by Therapy With an Anti–CD3–Like Monoclonal Antibody", *Transplantation*, 55, 459–468, (1993).

N. Ogasa, et al., "Altered Expression of Cytokine Genes by CD45RB Monoclonal Antibody in Renal Allograft Rejection", Transplantation Proceedings, 27, No. 1, 398, (Feb., 1995).

Ortho MultiCenter Transplant Study Group. "A Randomized Clinical Trial of OKT3 Monoclonal Antibody for Acute Rejection of Cadeveric Transplants", *N. Eng. J. Med.*, 313, 337–342, (Aug., 1985).

T. C. Pearson, et al., "Lymphocyte Changes Associated with Prolongation of Cardiac Allograft Survival in Adult Mice Using Anti–CD4 Monoclonal Antibody", *Clin. Exp. Immunol.*, 92, 211–217, (1993).

T. C. Pearson, et al., "The Assessment of Transplantation Tolerance Induced by Anti–CD4 Monoclonal Antibody in the Murine Model", *Transplantation*, 55, 361–367, (Feb., 1993).

N. Perico, et al., "Toward Novel Antirejection Strategies: In Vivo Immunosuppressive Properties of CTLA4Ig", *Kidney International*, 47, 241–246, (1995).

S. Poppema, et al., "Antobody MT3 is Reactive with a Novel Exon B–Associated 190–Da Sialic Acid–Dependent Epitope of the Leukocyte Common Antigen Complex", *The Journal of Immunology*, 147, No. 1, 218–223, (Jul., 1991).

J. A. Powelson, et al., "CDR–Grafted OKT4A Monoclonal Antibody in Cynomolgus Renal Allograft Recipients", *Transplantation*, 57, 788–793, (Mar., 1994).

G. Sandberg, "Anti–Lymphocyte Serum", *Encyclopedia of Immunology*, Academic Press, London, Roitt, I. M., ed., 142–144, (Dec., 1992).

P. Sempe, et al., "In Vivo Treatment With Monoclonal Antibodies", Imhof, B., 'Lymphatic Tissues in Vivo Immune Responses', Dekker, New York, 649–653, (1991).

P. Sempe, et al., "Role of CD4+CD45RA+T Cells in the Development of Autoimmune.Diabetes in the Non–Obese Diabetic (NOD) Mouse", *Intern Immunol.*, 5, 479–489, (1993).

F. W. Shen, "Monoclonal Antibodies To Mouse Lymphocyte Differentiation Alloantigens", 25–31, (1981).

I. Stamenkovic, et al., "The B Lymphocyte Adhesion Molecule CD22 Interacts with Leukocyte Common Antigen CD45RO on T Cells and alpha2–6 Sialyltransferase, CD75, on B Cells", *Cell*, 66, 1133–1144, (Sep., 1991).

T. A. Waldmann, "Monoclonal Antibodies in Diagnosis and Therapy", *Science*, 252, 1657–1662, (Jun., 1991).

H. Yakura, et al., "Alleviation of Autoimmunity in BXSB Mice by Monoclonal Alloantibody to Ly–5 (CD45)", *Eur. J. Immunol.*, 19, 1505–1508, (1989).

H. Yakura, et al., "On The Function Of Ly–5 In The Regulation Of Antigen–Driven B Cell Differentiation", *J. Exp. Med.*, 157, 1077–1088, (1983).

Z. Zhang, et al., "Prevention and Reversal of Renal Allograft Rejection by Monoclonal Antibody to CD45RB in the Mouse Model", Transplantation Proceedings, 27, 389, (Feb., 1995).

USE OF ANTI-CD45 LEUKOCYTE ANTIGEN ANTIBODIES FOR IMMUNOMODULATION

CROSS REFERENCE TO RELATED APPLICATIONS

This application is a continuation-in-part of U.S. application Ser. No. 08/423,843 filed Apr. 18, 1995, which in turn is a continuation-in-part application of U.S. Ser. No. 08/071,009 filed Jun. 2, 1993, now abandoned, both of which are herein incorporated by reference.

BACKGROUND OF THE INVENTION

Organ, cell and tissue transplant rejection and the various autoimmune diseases are thought to be primarily the result of a T-cell mediated immune response. This T-cell mediated immune response is initially triggered by helper T-cells which are capable of recognizing specific antigens. These helper T-cells may be memory cells left over from a previous immune response or naive cells which are released by the thymus and may express any of an extremely wide variety of antigen receptors. When one of these helper T-cells recognizes an antigen present on the surface of an antigen presenting cell (APC) or a macrophage in the form of an antigen-MHC complex, the helper T-cell is stimulated to produce IL-2 by signals emanating from the antigen-specific T-cell receptor, co-receptors, and IL-1 secreted by the APC or macrophage. The helper T-cells then proliferate. Proliferation results in a large population of T-cells which are clonally selected to recognize a particular antigen. T-cell activation may also stimulate B-cell activation and nonspecific macrophage responses.

Some of these proliferating cells differentiate into cytotoxic T-cells which destroy cells having the selected antigen. After the antigen is no longer present, the mature clonally selected cells will remain as memory helper and memory cytotoxic T-cells, which will circulate in the body and recognize the antigen should it show up again. If the antigen triggering this response is not a foreign antigen, but a self antigen, the result is autoimmune disease; if the antigen is an antigen from a transplanted organ, the result is graft rejection. Consequently, it is desirable to be able to regulate this T-cell mediated immune response.

CD45 antigen (CD45) is expressed on most leukocytes. Indeed, it was previously thought that a common CD45 antigen was present on all leukocytes, for which reason the receptor was originally known as the Leukocyte Common Antigen (LCA). Monoclonal antibodies (mAbs) to CD45 were proposed as a means of effectively eliminating all leukocytes where desirable, for example, purging an organ to be transplanted of passenger leukocytes prior to transplantation using nonspecific CD45 monoclonal antibody. See, e.g., WO 91/05568.

It has recently been shown that different isoforms of CD45 are generated by alternate splicing of a single primary transcript of the CD45 gene. These CD45 isoforms include CD45RA, CD45RB, CD45RC, and CD45RO. CD45RA contains the expression product of exon 4 (sometimes referred to as $R^A$) of the CD45 gene; CD45C contains the expression product of exon 6; CD45RB contains the expression product of exon 5; CD45RO does not contain the expression products of any of the three exons 4, 5, or 6. See Hall et al, "Complete Exon-Intron Organization of the Human Leukocyte Common Antigen (CD45) Gene," *J. Immunol.*, 141, 2781(1988), herein incorporated by reference and Streuli et al, "Characterization of CD45 and CD45R Monoclonal Antibodies Using Transfected Mouse Cell Lines that Express Individual Human Leukocyte Common Antigens," *J. Immunol.*, 141, 3910 (1988). The significance of this variable expression, however, has been unclear.

Increased success in clinical organ transplantation has paralleled improvements in techniques for immunosuppression. However, increasingly potent immunosuppressant drugs often produce complications due to their lack of specificity. For example, recipients can become very susceptible to infection. Highly specific immunosuppression is therefore desired.

The ideal specific immunosuppression method would be a treatment which suppresses the action of the lymphocytes responsible for rejection of the particular graft the patient receives without otherwise affecting the immune system.

Therefore, a need exists to durably and selectively suppress or otherwise modulate the immune response in humans, particularly transplant recipients or those afflicted with autoimmune diseases.

SUMMARY OF THE INVENTION

The present invention provides a method for in vivo immunosuppression in humans and mammals. The methods include pretreatment in vivo therapies to prevent rejection of transplanted cells, tissues and organs and post-transplant in vivo therapies to reverse a pathological immune response. Preferably, the present method can impart durable tolerance, rather than just delayed rejection to the recipient. The methods also include in vivo treatment of autoimmune diseases.

Specifically, the method of the present invention comprises administering to a patient in need of such treatment, an effective immunosuppressive amount of at least one compound which binds specifically to a CD45 leukocyte antigen present on T-cells. For example, the method of the present invention can be used to treat a patient undergoing transplant rejection, including graft-versus host disease or afflicted with an autoimmune disease. Preferably, the compound binds to the CD45RB receptor. The present invention additionally provides pharmaceutical compositions comprising an effective immunosuppressive amount of at least one compound which specifically binds to a CD45 antigen in combination with a pharmaceutically acceptable carrier. The term "compound" is meant to indicate, for example, antibodies as defined herein, and molecules having antibody-like function such as synthetic analogues of antibodies, e.g., single-chain antigen binding molecules, small binding peptides, or mixtures thereof.

Preferably, the compound of the present method is an antibody. More preferably, the antibody administered will be capable of binding to the CD45RB leukocyte antigen, the CD45RO leukocyte antigen, the CD45RA leukocyte antigen or the CD45RC leukocyte antigen. Most preferably, the antibody is capable of binding to the CD45RB or CD45RO leukocyte antigen.

As mentioned hereinabove, the method of the present invention is useful in the treatment of transplant rejection. More specifically, the method may be employed for the treatment of a patient that has undergone cell tissue or organ transplantation that is either allogeneic or xenogeneic. Furthermore, the method of the present invention may be utilized prior to, following or concurrently with the transplant procedure, or any combination thereof.

The method of the present invention is contemplated to be beneficial in a variety of transplant situations, even those situations where a recipient may receive sequential transplants of the same or different cells, tissues, or organs. For example, the method of the present invention may be utilized during a heart, liver, bone marrow or kidney transplant, or during the transplantation of pancreatic islets or vascular tissue, e.g., a coronary bypass procedure.

The method of the present invention may also be useful in the treatment or prevention of autoimmune disease, inflammatory conditions and arthritic or rheumatoid diseases. For example, the method of the present invention may be employed for the treatment of autoimmune hematological disorders, systemic lupus erythematosus, inflammatory bowel disease, ulcerative colitis, Crohn's disease, multiple sclerosis, diabetes mellitus type 1, and the like.

In a further embodiment of the method of the present invention, an anti-inflammatory or immunosuppressive drug may be administered prior to, following, or concurrently with the compound described hereinabove. For example, suitable drugs for this purpose include, but are not limited to, cyclosporin, FK-506, rapamycin, corticosteroids, cyclophosphamide, mycophenolate, mofetil, leflunomide, anti-lymphocytc globuline, deoxyspergualin OKT-3 and the like.

In yet another embodiment, the method of the present invention may further comprise administering an amount of the patient's lymphocytes to the patient, i.e., in combination with the CD45 leukocyte antigen binding compound(s).

This invention is based on the discovery that leukocytes such as different types of T lymphocytes, or "T-cells" may predominantly express one or another CD45 isoform. Naive helper T-cells and memory T-cells express predominately CD45RA and CD45RO respectively. CD 45RB expression is also variable; it is highly expressed (bright) on naive helper T-cells (Th0) and on T-cells that produce predominantly interleukin 2 and can induce inflammatory and cytotoxic responses (Th1). T cells that predominantly produce interleukin 4 and induce humoral immune responses (Th2) have low CD45RB expression (dim).

It has now been shown that some antibodies which react with CD45RB (MB23G2 in mouse, 6G3 in primates) are capable of selectively inhibiting the inflammatory and cytotoxic T-cell mediated immune response without destroying the pool of memory T-cells. Consequently, CD45RB suppressors have a great advantage over current immunosuppressants in that (i) they act on a particular T-cell population rather than having an overall immunosuppressive effect, thereby avoiding the risk of side effects associated with over-suppression of the immune system; and (ii) they are capable of conferring long term tolerance to a particular antigen when they are administered contemporaneously with exposure to antigen, e.g., just before and after an organ transplant or during an acute phase of an autoimmune disease.

As used herein, the term "immune tolerance" or simply "tolerance" is intended to refer to the durable active state of unresponsiveness by lymphoid cells to a preselected or specific antigen or set of antigens. The immune response to other immunogens is thus unaffected, while the requirement for sustained exogenous immunotherapy is either reduced or is eliminated. Additionally, tolerance enables subsequent transplantation of material comprising the same antigen or set of antigens without increasing the need for exogenous immunotherapy.

Generally, it is believed that the present methods may lead to T-cells having a receptor for the antigen becoming anergized, so that the T-cell clones are functionally, if not actually, deleted. For a fully functional activation of T-cells two signals are necessary. The first signal requires recognition of an antigen via the T-cell receptor. The second signal requires interaction between co-stimulatory molecules, such as B7, on antigen presenting cells and receptors, such as CD28, on the T-cells. It is generally accepted that lack of this second signal through CD28 leads to anergy. However, CD45 is required for the activation through the T-cell receptor and interference with this process through CD45RB interrupts the first signal and can also lead to anergy. This is in fact a more fundamental approach than blocking of the B7-CD28 interaction, since there are a number of different co-stimulatory pathways, whereas there is only the one T-cell receptor complex. Since CD45 is differentially expressed it is also possible to selectively affect specific subsets of T-cells. Thus, the observed effects are not due solely to depletion of a subset, or of the general T-cell population, but rather involve a combination of transitory depletion and a durable effect that leads to tolerization of the recipients. For example, in a mouse kidney transplant model, allograft tolerance following initial treatment with anti-CD45RB monoclonal antibody persists indefinitely, with survival well in excess of 100 days. In mice surviving over 100 days following a kidney allograft, the present method permits skin grafts syngeneic with the donor kidney to be tolerated, while skin grafts allogeneic with both the recipient and the donor kidney were rejected.

The term "antibody", includes human and animal mAbs, and preparations of polyclonal antibodies, as well as antibody fragments, synthetic antibodies, including recombinant antibodies, chimeric antibodies, including humanized antibodies, anti-idiotopic antibodies and derivatives thereof.

As used herein, the term "treating", with respect to an autoimmune disease or condition includes preventing the onset or flare-up of the disease or condition, as well as reducing or eliminating one or more symptoms of the disease or condition.

DETAILED DESCRIPTION OF THE INVENTION

Figure 1:
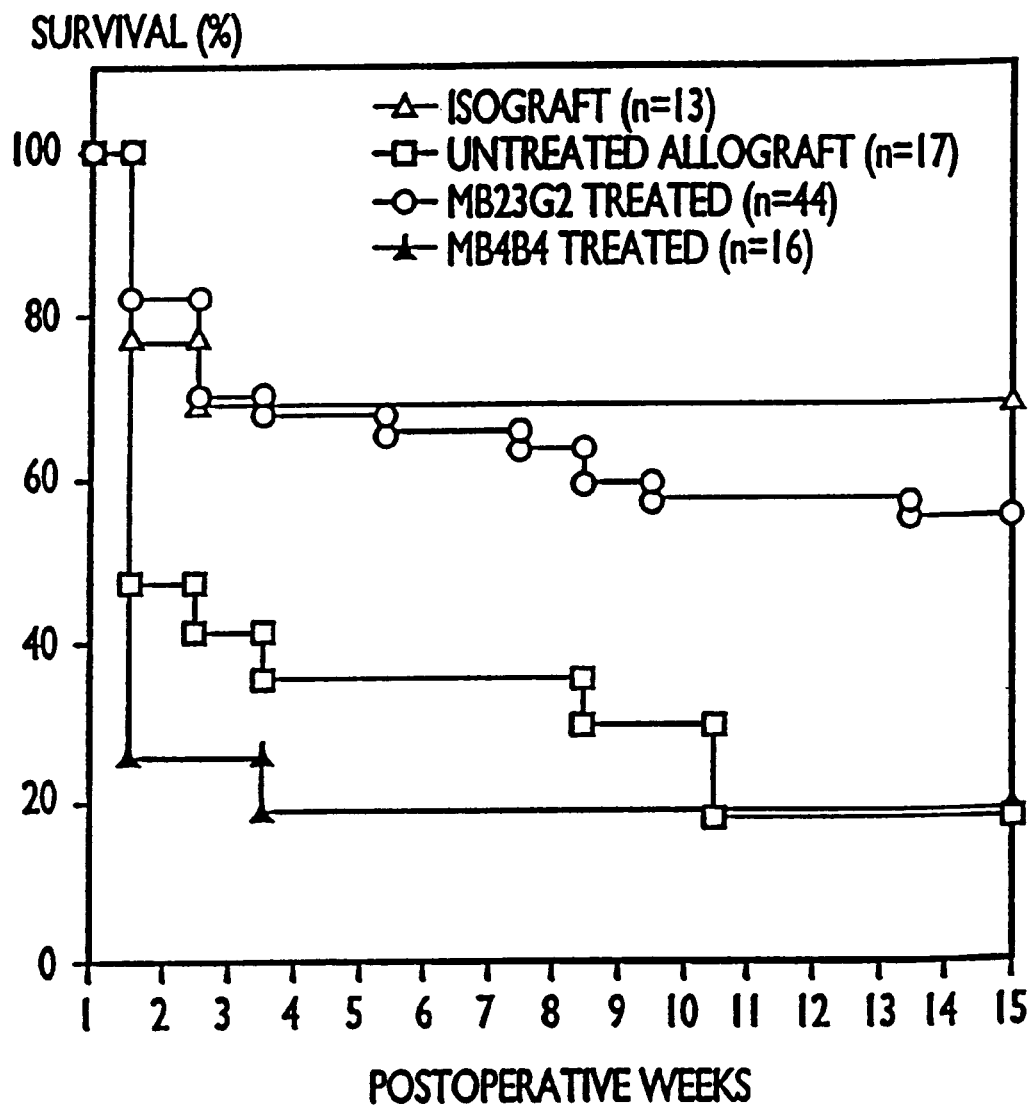
FIG. 1 shows prolonged survival of MB23G2—treated animals compared to an untreated group.

The compounds, antibodies and compositions of the invention are preferably produced as described in the following examples, or by equivalent means as would be apparent to one skilled in the art.

It will be understood by those skilled in the art that the hybridomas herein referred to may be subject to genetic mutation or other changes while still retaining the ability to produce monoclonal antibody of the same desired specificity. The present invention therefore encompasses mutants, other derivatives and descendants of the hybridomas.

It will be further understood by those skilled in the art that a monoclonal antibody can be subjected to the techniques of recombinant DNA technology to produce other derivative antibodies, humanized or chimeric molecules or antibody fragments which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, GB 2188638A, both herein incorporated by reference).

Antibodies Against CD45R Isoforms

S. Poppema, et al., *J. Iminunol.*, 147, 218 (1991), previously described the monoclonal antibody MT3. This publication, however, does not disclose a detailed method for making this antibody, nor does it disclose any pharmnaceutical use for this antibody and, therefore, necessarily fails to disclose the T-cell population recognized by this antibody. A. Lazarovits, et al., *Transplantation*, 54, 724 (1992), characterized the in vitro effect of this antibody. Lazarovits et al., for the first time, showed that MT3 mAb inhibits proliferation of and generation of T-cells by interfering with CD45RB. In addition to MT3 mAb, Lazarovits et al. reported that monoclonal antibodies to CD45RB, such as an antibody produced by the cell line HB220 which is publicly available from the ATCC in Rockville, Md. (now designated anti-CD45RB mAb (MB23G2)), bind to CD45RB and are effective agents in inhibiting immune function in vitro and in vivo (see U.S. Ser. No. 08/071,009 filed Jun. 2, 1993 herein incorporated by reference).

The inventors have now found that 6G3 monoclonal antibody binds to CD45RB. This is a murine IgG1 directed against human CD45RB. It cross-reacts with monkey CD45RB. The inventors have also now found that the MB23G2, 6G3, and MT3 monoclonal antibodies bind to neuraminidase sensitive epitopes on leukocytes including T-cells and that at least MB23G2 and 6G3 increase the tyrosine phosphorylation of phospholipase C-γ1. It is of interest to note that HB223 (now designated MB4B4), an analogous anti-CD45RB antibody to those of the invention, is found not to bind to neuraminidase sensitive epitopes. It is also observed that MB4B4 mAB binds to a neuraminidase insensitive epitope and does not alter the tyrosine phosphorylation of phospholipase C-γ1. MB4B4 was also ineffective at preventing renal allograft rejection in mice. The specific anti-CD45R mAbs that can be used in the summarized present invention are in Table I, hereinbelow; from Streuli et al., *J. Immunol.*, 141, 3910 (1988) which is incorporated herein by reference.

TABLE I

Classification of Anti-CD45R mAb[a]

| | |
|---|---|
| CD45RC | DNL-1.9[c], OX22 |
| CD45RA | Anti-2H4[b], 3AC5, F8-11-13, E7, HI 100[c], CMRF.11 73.5.17, G1-15, 10G3, 111-1C5, Leu18, 2A10, 5A9 MMT-1, 5E7, 4F4, HB-11 |

TABLE I-continued

Classification of Anti-CD45R mAb[a]

| | |
|---|---|
| CD45RO | UCHL1[c] |
| CD45RB | PD-7/26/16, 6B6[c], 6G3, MT3, MEM93[d], MB2362, MB4B4 |

[a]Anti-CD45R antibodies were classified into three groups: CD45RA, CD45RO, and CD45RB, based on their binding to the 300-19(LCA) cell lines.
[b]Available from Coulter, Nialeah, FL.
[c]Available from Pharmingen, San Diego, CA
[d]See Bazil et al., Immunogenetics, 29, 202 (1989).

Chimeric and Reshaped Antibodies

EP-A-0 120 694 (Boss et al/Celltech, herein incorporated by reference) describes the cloning and expression of chimeric antibodies. In these derivatives, the variable domains from one immunoglobulin are fused to constant domains from another immunoglobulin. Usually, the variable domains are derived from an immunoglobulin gene from one species, for example a mouse or a rat, and the constant domains are derived from an immunoglobulin gene from a different species, perhaps a human. This technology is now very well known in the art. A later European Patent Application, EP-A-0 125 023 (Cabilly/Genetech, herein incorporated by reference), also U.S. Pat. No. 4,816,567, describes much the same subject as the Boss patent application, but describes production of other variations of immunoglobulin-type molecules using recombinant DNA technology.

Another possibility is to attach just the variable region of the monoclonal antibody to another non-immunoglobulin molecule, to produce a derivative chimeric molecule (see WO 86/01533, Neuberger and Rabbits/Celltech, herein incorporated by reference). A further possibility would be to produce a chimeric immunoglobulin having different specificities in its different variable regions, e.g., the monoclonal antibodies of the present invention (see EP 68763A). Yet another possibility would be to produce a mutation in the DNA encoding the monoclonal antibody, so as to alter certain of its characteristics without changing its essential specificity. This can be done by site-directed mutagenesis or other techniques known in the art.

The Winter patent application EP-A-0 239 400 (herein incorporated by reference) describes how it is possible to make an altered, derivative, antibody by replacing the complementarity determining regions (CDRs) of a variable region of an immunoglobulin with the CDRs from an immunoglobulin of different specificity, using recombinant DNA techniques—so called "CDR-grafting". This enables altering the antigen-binding specificity of an antibody. (In the present case it might be the CDRs of MT3, 6G3, MB23G2, an antibody with the same binding specificity as these anti-CD45RB antibodies, or an antibody which is cross-reactive with MT3, 6G3, or MB23G2 which are transferred to another antibody.) Thus, CDR grafting enables "humanization" of antibodies, in combination with alteration of the framework regions.

Human antibodies can also be directly provided by reconstituting the human immune system in mice lacking their native immune system, then producing human antibodies in these "humanized mice."

A "humanized" antibody containing the CDRs of a rodent antibody specific for an antigen of interest might well be less likely to be recognized as foreign by the immune system of a human. It follows that a "humanized" antibody with the same binding specificity as, e.g., MT3 or 6G3, or an antibody that cross-reacts with either (see later), might well be of particular use in human therapy and/or diagnostic methods.

As discussed, the state of the art is such that the person skilled in the art well knows how to manipulate and alter any given antibody or gene(s) encoding for the same to generate a derivative to suit his or her particular needs.

Anti-idiotopic Antibodies

The provision of an antibody such as MT3 or 6G3 allows persons skilled in the art to obtain binding partners, e.g., antigens/epitopes or antibody/paratopes which bind to it. Therefore, the present invention also provides binding partners, e.g., antigens and/or antibodies which bind with an antibody or derivatives thereof as hereby provided, such as MT3 and 6G3.

The binding partners obtained by use of the MT3 mAb and 6G3 mAb may also be used to produce additional ligands, e.g., antibodies other than MT3 or 6G3 (or molecules having antibody-like binding function, e.g., fragments, derivatives and synthetic analogues of antibodies such as single-chain antigen-binding molecules). Therefore, also provided are ligands, e.g., mAbs which are able to bind with a binding partner which is able to bind with the MT3 mAb and 6G3 mAb. Such ligands ("cross-reactive ligands"), e.g., mAbs may recognize the same epitope as recognized by MT3 mAb and 6G3 mAb on said binding partner.

The present invention also provides derivatives, functional equivalents (e.g., a molecule having an antibody-like binding specificity) and fragments of said cross-reactive ligands, perhaps produced using one or more of the techniques of recombinant DNA technology referred to and discussed above. Also included are single domain ligands (mAbs) as described in WO 90/05144 (herein incorporated by reference).

Antigen Isolation

Using standard techniques, it is possible to use a ligand, e.g., antibodies of the present invention and derivatives thereof, in immunopurification of a binding partner antigen. Techniques for immunoaffinity column purification are well known, see for instance "Current Protocols in Immunology," ed. J. E. Coligan et al, John Wyley and Sons, Unit 8.2 (herein incorporated by reference). For instance, it is now known that the epitope identified by the CD45RB mAb MB23G2 is encoded by the B exon of the leukocyte common antigen gene. Isolation of the epitope and compounds binding to the epitope are contemplated by this invention.

In fact, it should be possible to use an immunoaffinity column to isolate cross-reactive ligands as discussed above, without needing to isolate the antigens themselves. A first round of immunoaffinity purification uses a ligand, e.g., MT3, 6G3, etc. mAb to remove from a sample the antigen-containing binding partner, which may then be used in the column to select, from a heterogeneous population of ligands, those ligands which are cross-reactive with the MT3 mAb, 6G3 mAb, etc. and recognize the same binding partners.

A binding partner, such as a peptide or small binding molecule, isolated using the ligand, e.g., the MT3, 6G3, etc. mAb may be used to select cross-reactive ligands from a repertoire or heterogenous population of antibodies generated by a whole variety of means. One way is to select monoclonal antibodies and cell lines producing them by the standard hybridoma techniques. Also provided by the present invention are immortalized cells, e.g., hybridomas producing said cross-reactive ligands.

Another way of selecting ligands which are cross-reactive with a ligand such as the MT3 mAb or 6G3 mAb is to use the methods for producing members of specific binding pairs disclosed in WO 92/01047 (Cambridge Antibody Technology Limited and MRC/McCafferty et al, herein incorporated by reference). This publication discloses expression of polypeptide chain components of a genetically diverse population of specific binding pair members, such as antibodies, fused to a component of a secreted replicable genetic display package (RGDP), such as a bacteriophage, which thereby displays the polypeptide on the surface. Very large repertoires of displayed antibodies may be generated, and screened by means of antigen binding to obtain one or more antibodies of interest, along with their encoding DNA. DNA encoding for a polypeptide displayed on the surface of an RGDP is contained within the RGDP and may therefore be easily isolated and cloned for expression. The antibody repertoire screen may of course be derived from a human source.

Recombinant Antibodies

Obviously, once one has an immortalized cell line, e.g., a hybridoma, or an RGDP containing DNA encoding at least a polypeptide component of a binding ligand, one skilled in the art is in a position to obtain (according to techniques well known in the art, see EPA 449,769) the entire nucleotide sequence encoding the ligand, e.g., the mAb secreted by the cell. Therefore, the present invention also encompasses primary nucleotide sequences which encode the ligands, e.g., mAbs as defined above, together with fragments of these primary sequences and secondary nucleotide sequences comprising derivatives, mutations and hybridizing partners of said primary nucleotide sequences.

These nucleotide sequences may be used in a recombinant system to produce an expression product according to standard techniques. Therefore, the present invention includes vectors (cloning and expression vectors) incorporating said nucleotide sequences, transformed cells incorporating said vectors and expression products produced by use of a recombinant system utilizing any such vectors or transformed cells.

The production of fusion proteins is also contemplated. See, for instance, Stamenkovic et al, "The B Lymphocyte Adhesion Molecule CD22 Interacts with Leukocyte Common Antigen CD45RO on T Cells and α2-6 Sialytransferase, CD75, on B Cells," CELL, Vol. 66, pp. 1133–1144 (1991), herein incorporated by reference.

The present invention also includes methods for expressing a ligand, e.g., a mAb, derivative, functional equivalent or fragment thereof, which comprises using a nucleotide sequence, vector or transformed cell as defined above.

More specifically, MT3 and 6G3 which are mAbs directed against the human CD45RB antigen will bind to an epitope on CD45RB in human cells expressing CD45RB. This epitope may then be purified, for instance utilizing an immunoaffinity column (as discussed), and partially or wholly sequenced, for instance using repeated rounds of Edman degradation.

Immunosuppression and Inducing Immune Tolerance

The antibodies and pharmaceutical compositions of the invention are useful in immunomodulation, especially immunosuppression, e.g., in the following indications:

a) Treatment and prevention of organ, cells or tissue allo-or xeno-transplant rejection, e.g., for the treatment of human recipients of, e.g., heart, lung, islets, bone marrow, chromaffin or dopamine producing cells, combined heart-lung, liver, kidney, pancreatic, skin, small bowel, vascular tissue grafts or corneal transplants. They are also indicated for the prevention of graft-versus-host disease (GvH), such as sometimes occurs following bone marrow transplantation. The methods and compositions of the invention also reverse and prevent rejection of organ transplants in mammals such as rodents and primates. For example, the antibodies prevent mice from rejecting kidney transplants and induce long term survival.

b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the methods of the invention may be employed include, autoimmune hematological disorders (including, e.g., hemolytic anemia, aplastic anemia, pure red cell anemia and idiopathic thrombocytopenia), systemic lupus erythematosus, polychondritis, scleredema, Wegener granulomatosis, dermatomyositis, chronic active hepatitis, myasthenia gravis, psoriasis, Steven-Johnson syndrome, idiopathic sprue, autoimmune inflammatory bowel disease (including, e.g., ulcerative colitis and Crohn's disease) endocrine ophthalmopathy, Graves disease, sarcoidosis, multiple sclerosis, primary biliary cirrhosis, juvenile diabetes (diabetes mellitus type 1), uveitis (anterior and posterior), keratoconjunctivitis sicca and vernal keratoconjunctivitis, interstitial lung fibrosis, psoriatic arthritis, glomerulonephritis (with and without nephrotic syndrome, e.g., including idiopathic nephrotic syndrome or minimal change nephropathy) and juvenile dermatomyositis.

c) Treatment of leukemias characterized by overproliferation of T-lymphocytes, including virally induced leukemias, e.g., HTLV-1-induced leukemia and acute lymphocytic leukemia.

Dosages and Dosage Forms

The invention provides a kit containing one or more compounds capable of binding to CD45 for administration to patients who have received xenografts. The kit can include said compounds in an appropriate pharmaceutical formulation such as a unit dosage form, along with one or more drugs used to suppress rejection induced by preexisting antibodies. Such drugs could include cyclophosphonamide, Deoxyspergualin and the like.

Appropriate dosages of said compounds will of course vary, e.g., depending on the condition to be treated (for example the disease type or the nature of resistance), the effect desired, and the mode of administration. Dosages effective in humans can be derived from dosages effective in mice and other mammals by methods known to the art, i.e., U.S. Pat. No. 5,035,878.

In general however satisfactory results are obtained on administration parenterally, e.g., intravenously, for example by iv drip or infusion, at dosages on the order of from 0.01 to 2.5 up to 5 mg/kg, e.g., on the order of from 0.05 or 0.1 up to 1.0 mg/kg. Suitable dosages for human patients are thus on the order of from 0.5 to 125 up to 250 mg iv, e.g., on the order of from 2.5 to 50 mg i.v. The compounds may be administered daily or every other day or less frequently at diminishing dosages to maintain a minimum level of compound in the blood during the antigen challenge, e.g., following organ transplant or during the acute phase of an autoimmune disease.

The pharmaceutical compositions of the present invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinized blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.50% by weight of the saline solution.

In clinical tests, for example, patients about to undergo kidney, liver or heart transplantation are selected for prophylactic therapy. On the day of transplantation, 2 hours prior to surgery, a first intravenous infusion of the compound, antibody or mixture thereof, is administered at a dose of 0.2 mg of each compound or antibody per kg of body weight. Two days after surgery an identical infusion of the compound and/or antibody at 0.4 mg/kg of body weight is administered and then repeated at weekly intervals for one month. The intravenous infusions are prepared as follows: the lyophilized compounds and/or antibodies are mixed together and dispersed into 100 ml sterile buffered saline containing 4.51% by weight of human albumin. This saline dispersion is administered to the patients over a 30 minute period.

The compounds of the invention are also useful as diagnostic aids, as diagnostic reagents or as components of a diagnostic kit to identify particular sub-populations of leukocytes. The compounds may be labeled, e.g., fluorolabeled or radiolabeled, using conventional techniques. For example, 25 micrograms of monoclonal antibody in 0.25 ml of 0.12 M sodium phosphate, pH 6.8 is iodinated using 2 mCi $^{125}$I and 10 micrograms chloramine T. After 5 minutes at 23° C., the reaction is stopped by the addition of 20 micrograms of sodium metabisulfite, 3 mg of KI and 1 mg of BSA. Iodinated protein is separated chromatographically. The labeled compounds are exposed to a frozen tissue section, e.g., from a patient exhibiting symptoms of graft rejection or acute autoimmune disease, exhibiting infiltration of leukocytes. Excess compound is washed away, and bound compound is assayed. Substantial binding of the compounds to leukocytes present in the tissue section suggests that the majority of leukocytes involved are naive rather than memory leukocytes, thereby indicating that therapy with the compounds and/or with immunosuppressants acting primarily on the T-cell mediated immune response, e.g., Cyclosporin or FK-506, is appropriate.

Finally, the compounds are useful in a screening assay to identify drugs capable of modulating the biological activity of CD45RB.

Adjuvant Agents

It is also contemplated that an anti-CD45 CD4RB compound may be given alone or with standard immunosuppressant or anti-inflammatory agents. These would include cyclosporin, FK-506, Leflunomide, Rapamycin, cyclophosphamide, mycophenolate mofetil, Deoxyspergualin, corticosteroids, anti-lymphocyte globulin, OKT-3 and the like, and others. Use of the compounds and/or antibodies of the invention is expected to reduce the dosage requirements for such drugs and thereby to reduce undesired side effects. The compounds may also be used in combination with other monoclonal antibodies or other compounds specifically recognizing particular lymphocyte sub-populations, e.g., CD25 mAbs, CTLA4-Ig fusion peptide, etc.

Ex Vivo, Conditioning of Recipient's Lymphocytes

In some cases, immune suppression and/or tolerization may be enhanced by administering an amount of lymphocytes derived from the recipient that have been conditioned in vivo or ex vivo with the anti-CD45R antibodies useful in the present invention. The conditioned or anergized lymphocytes can be given before, simultaneously with, or following transplantation and/or administration of the anti-CD45R antibodies, in an amount effective to induce or assist in inducing immune tolerance in the recipient. The lymphocytes preferably are obtained from the recipient prior to transplantation or other treatment, preconditioned by exposure to the antibodies employed in the present method, and exposed to the antigens on the donor material, prior to re-introduction into the recipient.

EXAMPLE 1

Murine Monoclonal Antibody to CD45RB

Murine monoclonal antibody to human CD45RB is produced by using conventional techniques, essentially as described by Kohler and Milstein in Nature 256: 49. Female BALB/C mice (20–25 g) each receive 100 µg of antigen containing human CD45RB, e.g., Hodgkin cell line DEV (publicly available), by i.p. injection. (Alternatively, the antigen may comprise murine cells which have been transformed to express human CD45RB). After 2 weeks a second booster injection comprising 50 µg of the antigen is administered, again by i.p. injection. The presence of antibodies reactive to the antigen in the animals' blood serum is confirmed by immunohistologic screening. Mice displaying maximum blood serum levels of CD45RB antibody receive another booster injection comprising 20 µg of antigen. Four days later, they are sacrificed and their spleen cells are isolated and fused with a suitable myeloma line, e.g., myeloma X63 (publicly available). The resulting hybridoma are cultured and selected for expression of antibody having a high affinity to CD45RB.

A hybridoma line producing murine monoclonal antibody to human CD45RB is the MT3 hybridoma line, which was deposited on Mar. 29, 1993 under the Budapest Treaty with the American Type Culture Collection (ATCC), 12301 Parklawn Drive, Rockville, Md. 20852/U.S.A.

A second hybridoma cell line, which produces rat monoclonal antibody to murine CD45RB, is HB220 (now designated MB23G2). This cell line has been deposited with the ATCC and is available by purchase from the ATCC.

A third hybridoma cell line (deposited with the ATCC as HB-11873), produces antibodies of the invention (6G3 mAb). This hybridoma cell line was produced by the fusion of myeloma cell line SP2/O and spleen cells from a mouse immunized with human large cell B cell non-Hodgkin lymphoma cell line VER. The resulting clones were screened by an immunoperoxidase procedure on frozen tissue sections of human tonsil and rhesus monkey spleen. Clone 6G3 was selected because of the high reactivity of 6G3 mAb with subsets of T and B lymphocytes in both tissues. The antibody reactivity of 6G3 was characterized as anti-CD45RB by its selective reactivity with human CD45RB expressing transfectants and by the characterization of the molecular weight of the antigen immunoprecipitated by 6G3 as three bands with molecular weights of 220, 204 and 190 kD. The reactivity of the antibody could be abolished by pretreatment of tissues, cells or blots with neuraminidase, indicating the sialic acid dependence of the antigen.

A fourth hybridoma cell line, HB223, produces analogous monoclonal antibodies to MB23G2; it is also deposited and available through the ATCC.

EXAMPLE 2

Chimeric Monoclonal Antibody to CD45RB a) Cloning of the Gene Encoding the Variable Domain of the Heavy Chain The genomic DNA of the desired hybridoma, in this example the MT3 or 6G3 hybridomas of Example 1, and of the parental myeloma cell lines of the hybridomas (myeloma X63 or SP2/O) is isolated and digested with EcoRI. Each digested DNA is then fractionated on the same agarose gel. After migration, the agarose gel is analyzed by Southern blot using as probe a $^{32}$P labeled 0.7 kb XbaI-EcoRI DNA fragment which encodes the murine heavy chain enhancer Eµ (Heinrich et al, J. OF IMMUNOL. (1989) 143: 3589) to identify the desired variable heavy chain fragment, i.e., the desired fragment is present in the MT3 and 6G3 hybridomas but not in the X63 or SP2/O myelomas. Further purification of this fragment is then carried out by preparative agarose gel electrophoresis.

DNA fragments of the same size as the desired fragment are cloned in the EcoRI restriction site of bacteriophage ZAP (Stratagene). Using the probe described above, the recombinant phages are screened and clones selected which hybridize to the probe. The DNA inserts of the selected clones are amplified on phage plate lysate by polymerase chain reaction (PCR) using as primers, a first oligonucleotide encoding the murine $J_Z$ gene and a second oligonucleotide encoding the beginning of the MT3 or the 6G3 heavy chain. The DNA fragments obtained from each of the selected clones are analyzed by Southern blot using as probe an oligonucleotide encoding a portion of the Eµ probe described above.

b) Construction of a Chimeric Heavy Chain Gene

The EcoRI fragment (comprising the gene of the MT3 or 6G3 heavy chain variable domain (including the promoter and the enhancer)) is obtained by digestion of the DNA of one of the phage clones selected in step a) is then cloned into the EcoRI restriction site of the eukaryotic expression vector pSV2 neo-human $\gamma_1$, constant part (Heinrich et al, supra). Following propagation of the resulting plasmid, the nucleotide sequence of the gene encoding the MT3 or 6G3 heavy chain variable domain is redetermined to exclude the possibility that a mutation in this gene has occurred.

c) Cloning of the Gene Encoding the Variable Domain of the Light Chain

The genomic DNA of the MT3 or 6G3 hybridomas and of the parental cell lines X63 or SP2/O is isolated and digested with EcoRI. Each digested DNA is then fractionated on the same agarose gel. After migration, the agarose gel is analyzed by Southern blot using as probe a $^{32}$P-labeled DNA fragment comprising the five mouse $J_K$ genes and the mouse $C_K$ gene. Size fractionated EcoRI fragments corresponding in size to the desired MT3 or 6G3 light chain variable domain are cloned in phage EMBL4 (Stratagene).

A clone containing the DNA fragment encoding the MT3 or 6G3 light chain is identified by screening the recombinant phage clones with the probe described immediately above. The desired DNA fragment is then subcloned into the EcoRI-XbaI site of pGEM4 (Promega) and its sequence determined.

d) Construction of a Chimeric Light Chain Gene

An XbaI—XbaI fragment containing the sequence encoding the murine heavy chain enhancer (Heinrich et al; supra) and a HindIII-SphI DNA fragment containing the sequence for the human κ constant part (huCκ) are cloned together into phage mpl8 (Stratagene). Site-directed mutagenesis is performed on the resulting recombinant phage to disrupt the HindIII site in the desired coding region and followed by digestion with EcoRI and HindIII to generate a DNA fragment containing the sequences for both (Eμ) and (huCκ). After filling in the ends of this fragment, the fragment is subcloned into the blunt-ended EcoRI-BamHI site of pSV2-DHFR to generate pSV2-DHFR-Eμ-huC$_κ$. The plasmid pSV2-DHFR is obtained by replacing the BamHI-HindIII fragment of pSV2-neo with a BamHI-HindIII fragment encoding the dihydrofolate reductase gene.

Lastly, an EcoRI-XbaI DNA fragment containing the MT3 or 6G3 light chain sequence is isolated from the recombinant pGEM4 plasmid of step 3 and subcloned into pSV2-DHFR-Eμ-huC$_κ$ to generate pSV2-DHFR-Eμ-huC$_κ$-MT3$_L$ or pSV2-DHFR-Eμ-huC$_κ$-6G3$_L$.

e) Expression of Chimeric Antibody

The plasmids obtained in steps b) and d) are co-transferred into the mouse myeloma cell line SP2/0 (ATCC CRL 1581) by electroporation using a gene pulser apparatus from Biorad. This technique is known to create stable transfectants at a high frequency. The SP2/0 cell line fails to produce endogenous heavy and light chains and is sensitive to Geneticin (G 418) at a concentration of 0.8 mg/l.

SP2/0 cells are grown in the usual growth medium (RPMI+10% FCS 5×10$_{-5}$ β-mercaptoethanol) harvested in the log phase of growth and washed with the electroporation buffer (Bio-Rad). Cell concentration is adjusted to 2×10$^7$ cells/ml. To 0.8 ml of the cell suspension is added 15–20 μg of each plasmid. The mixture is placed on ice and left to stand for 10 min. Then the cells are subjected to an electrical pulse (280 Volt; 25° F.) and again left to stand for 15 min. Cells are transferred to the usual growth medium and incubated at 37° C. in a $CO_2$ incubator.

After a 3-day incubation, selection for G 418 resistance is started. Cells are re-suspended in fresh medium containing 1.4 mg/ml G 418. The cultures yield growing cells after 10–14 days incubation in the presence of G 418. After the 2-week incubation, supernatants of the confluent cultures are tested for human IgG expression in a sandwich-type ELISA (anti-human κ-light chain/supernatant/anti-human IgG-alkaline phosphatase conjugate).

This test indicates that complete antibody molecules are secreted in all cultures at varying concentrations in the range of 50–500 ng/ml.

To select cells in which the DHFR gene is amplified and which therefore secrete high amounts of the desired antibody, two selection procedures for methotrexate (MTX) resistance are carried out as described below. For this purpose, the G 418 resistant cell pools are each divided and amplification is preformed either according to procedure A (MTX increase by a factor of 2 or 2.5) or procedure B (MTX increase by a factor of 5) (Table II).

TABLE II

| Procedure A | Procedure B |
| --- | --- |
| 100 nM MTX | 200 nM MTX |
| 250 nM MTX | 1 μM MTX |
| 500 nM MTX | 5 μM MTX |
| 1 μM MTX | 25 μM MTX |
| 2.5 μM MTX | 100 μM MTX |
| 5 μM MTX | |
| 10 μM MTX | |
| 25 μM MTX | |
| 100 μM MTX | |

Each amplification step comprises inoculating the cells at a density of 2×10$_5$ cells/ml in the usual growth medium supplemented with G 418 at 1.4 mg/ml and with MTX at the concentration of choice. After 72 hour incubation, cells and the supernatant are separated. Antibody secretion is monitored either by ELISA or by HPLC using a protein A column. Most of the pools reach a maximum of specific antibody production at a certain MTX concentration. The best producing pools are cloned by limiting dilution. Out of several hundred analyzed clones, 15 best producing clones are selected. Productivity of the clones ranges from 30 to 50 mg mAb/10$^9$ cells in 72 hours.

The antibody is purified from a culture supernatant by elution on a protein A affinity column.

EXAMPLE 3

In Vivo Prevention of Rejection of Kidney Transplants in Mice

In this experiment a right nephrectomy was performed on 18 mice at the same time an allograft (kidney transplant from a different strain of mouse) was performed. A contralateral nephrectomy was followed on the seventh postoperative day (POD 7), so that from that point on, the animals relied only on the allografted kidney. Nine of the mice were treated with 50 μg of a mixture of rat anti-mouse CD45RB monoclonal antibodies produced from cell lines HB220 and HB223 iv for the first two days (POD 0 and POD 1) followed by 100 μg of each antibody intraperitoneally (i.p.) for 9 days (POD 2 to POD 10). Of the nine control animals which did not receive the anti-CD45RB antibodies, seven were dead three days after the second kidney was removed, and the remaining two exhibited severe rejection one week later.

Of the nine animals treated with the anti-CD45RB antibodies, there were three deaths due to surgical complications unrelated to any immune response, but remarkably, the remaining six animals survived long term (e.g., over 100 days) without any further treatment and without any evidence of allograft rejection. In a third group of 10 untreated isograft recipients, the incidence of death due to surgical complication was the same. There was no significant difference between the serum creatinine levels of the allograft group receiving monoclonal antibody and the isograft group, indicating that the kidneys in both groups were functioning normally.

EXAMPLE 4

Reversal of the Rejection of Kidney Transplants in Mice

In this experiment a right nephrectomy was performed on 10 mice at the same time an allograft (kidney transplant from a different strain of mouse) was performed.

All ten of the animals were observed for five days without immunosuppression therapy. These animals were known to be experiencing severe rejection at this stage because sacrificed control animals, also subjected to a nephrectomy and an allograft kidney transplantation, exhibited severe rejection on day 5.

On POD 5, four of the animals were given three daily 25 μg doses, intraperitoneally, of anti-CD45RB antibody (a mixture of monoclonal antibodies from cell lines HB220 (anti-CD45RB MB23G2 mAb) and HB223 (anti-CD45RB MB4B4 mAb)) for the next three days. All four of the animals experienced rapid reversal of their rejection symptoms, including a return to normal levels of creatinine, and lived greater than 100 days. The untreated animals died by day nine due to organ rejection. Table III summarizes the results of this experiment:

TABLE III

REVERSAL OF THE REJECTION OF KIDNEY TRANSPLANTS IN MICE

| MOUSE | THERAPY | SURVIVAL DAYS | CAUSE OF DEATH |
|---|---|---|---|
| 1 | NONE | 8 | REJECTION/UREMIA |
| 2 | NONE | 9 | REJECTION/UREMIA |
| 3 | NONE | 8 | REJECTION/UREMIA |
| 4 | NONE | 9 | REJECTION/UREMIA |
| 5 | NONE | 9 | REJECTION/UREMIA |
| 6 | NONE | 9 | REJECTION/UREMIA |
| 7 | CD45RB | >100 | — |
| 8 | CD45RB | >100 | — |
| 9 | CD45RB | >100 | — |
| 10 | CD45RB | >100 | — |

This data with respect to reversal is significant in confirming that the antibody therapy is highly effective in suppressing an immune response. Treatment and cures are accomplished with antibody therapy.

EXAMPLE 5

Confirming Results Using MB23G2 and MB4B4 Separately for Kidney Transplants in Mice Recipient Balb/c (h-2d) mice had the right kidney removed before receiving a transplanted kidney from donor C57B1 (h-2b) mice. A left native nephrectomy was subsequently performed on day 7. There were four groups of animals. Thirteen received isografts, 17 received allografts with no immunosuppression (vehicle control), 44 received allografts and were given two doses of purified rat anti-mouse CD45RB mAb MB23G2 1 mg/kg (30 μg) intravenously on days 0 and 1, and 16 received allografts but were treated with two doses of purified rat anti-mouse CD45RB mAb MB4B4 1 mg/kg (30 μg) intravenously on days 0 and 1. No further antibodies were given.

Figure 2:
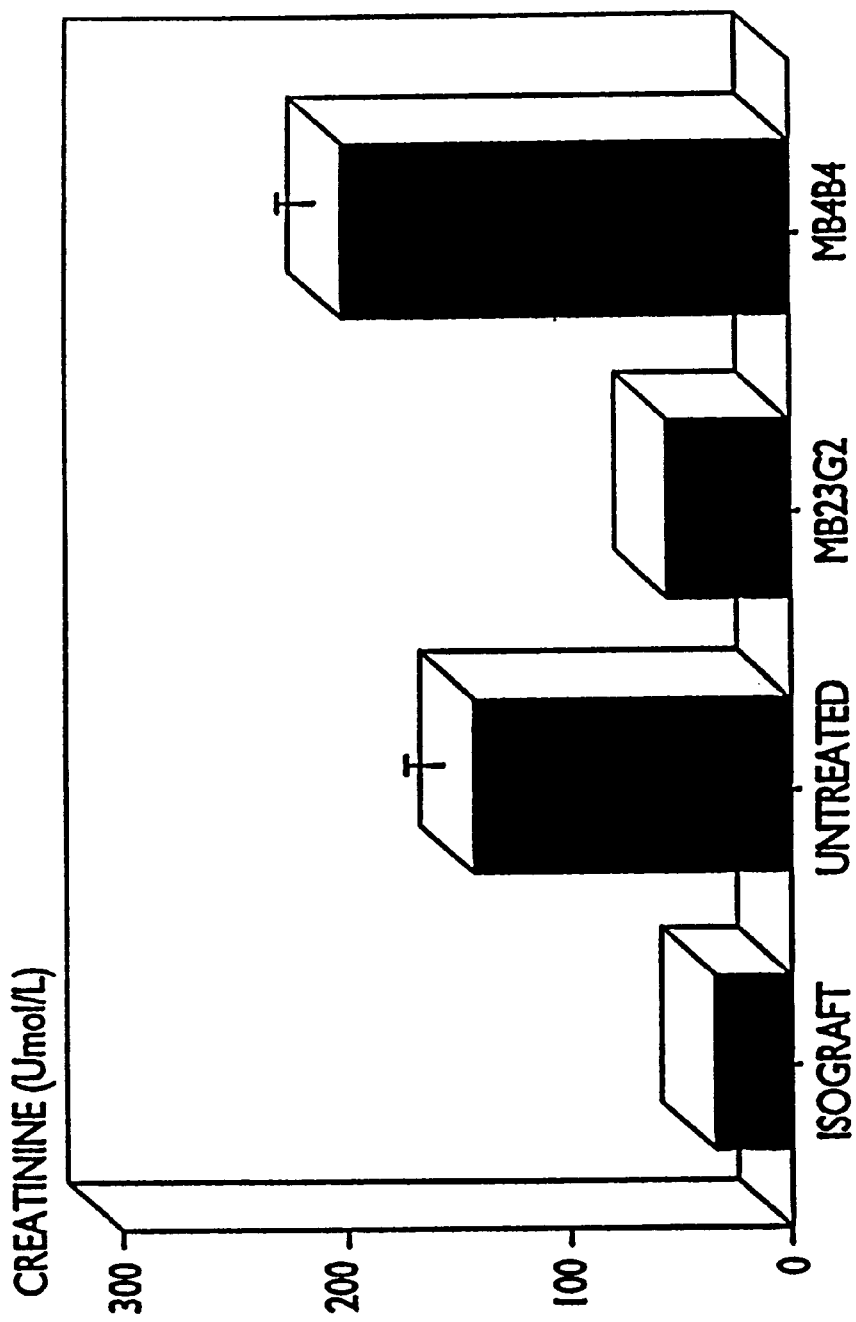
FIG. 2 shows the serum creatinine levels from each group at the time of sacrifice.

As expected, the MB23G2-treated animals exhibited prolonged survival compared to the untreated group (p<0.002) (see FIG. 1) and was comparable to the isograft group. Remarkably, the anti-CD45RB MB4B4 mAb was no better than the vehicle alone at preventing rejection. Both MB23G2 and MB4B4 are IgG2a but a difference exists between them. Both mAbs bind to Balb/C leukocytes as assayed by FACS. However, MB23G2 binding is inhibited by neuraminidase, while binding of MB4B4 is not affected by such treatment. FIG. 2 shows the serum creatinine levels in animals from each group at the time of sacrifice, or beyond day 100 for the long-term survivors. There were no differences between the isograft and MB23G2-treated groups, while the untreated and MB4B4-treated animals died from uremia. Therefore, the glycosylated epitope for MB23G2 is either involved in, or is near to, sites involved in the biochemical activity of CD45RB. The non-glycosylated epitope for MB4B4 appears to be non-critical for CD45RB activity.

Immunoperoxidase microscopic studies were performed on renal allografts at 7 days in three groups of mice: untreated, MB4B4-treated, and MB23G2-treated. Sections were stained with rat anti-mouse mAb reactive with mouse CD3, CD4, CD8, CD45RB and Ia. Slides were evaluated in a masked manner with respect to aggregates and diffuse infiltrates as described in Ibrahim et al., TRANSPLANTATION Vol. 59, pp. 724–728, herein incorporated by reference. The numbers of cells in the diffuse infiltrates were counted in ten (×400) high power fields (HPF) in each section of 5 mice per group and the data are shown in Table IV below.

TABLE IV

DIFFUSE CELLULAR INFILTRATES IN KIDNEY ALLOGRAFTS AT 7 DAYS (MEDIANS/HPF)

| Phenotype | mAb | Untreated | MB4B4-Treated | MB23G2-Treated |
|---|---|---|---|---|
| CD3 | KT3 | 33 | 38 | 22* |
| CD4 | GK1.5 | 10 | 11 | 9 |
| CD8 | 3.155 | 27 | 26 | 13* |
| CD45RB | MB23G2 | 12 | 10 | 9 |

*P <0.05. Statistically significant differences between MB23G2-treated and nontreated groups and between MB23G2-treated and MB4B4-treated groups.

Interestingly, differences between the three groups of mice became evident after separately counting cells in aggregates and diffuse infiltrates. Staining for Ia was clearly less in the MB23G2-treated allografts than in the other groups, but due to positive staining of other interstitial cell types the numbers of lymphocytes could not reliably be quantified. The aggregates contained high numbers of CD4+ and CD8+ cells in all three groups. While the numbers of CD4+ and CD45RB+ cells in the diffuse infiltrates were approximately equivalent in all three groups (Table III, second and fourth rows) the numbers of CD3+ cells and CD8+ cells in the diffuse infiltrates were statistically different between MB23G2-treated and the other groups (Table III, first and third rows). Thus, the MB23G2-treated animals demonstrated an elevated CD4:CD8 ratio compared to MB4B4-treated and untreated animals. Remarkably, few of the infiltrating cells were CD45RB positive, a particularly notable finding considering that the CD45RB mAb MB23G2 could reverse acute rejection.

EXAMPLE 6

Immunotolerance

To assess the possibility of antigen specific tolerance, skin transplants were performed on 13 animals from Example 5 which had maintained a kidney transplant beyond 100 days after receiving 2 doses of MB23G2 mAb at the time of renal allografting. Each animal received full thickness skin allografts from a C57B1/6 mouse (isogeneic with the donor of the renal allograft) and a control skin transplant: 9 received a Balb/C isograft and 4 received a CBA allograft (third party donor). No further immunosuppression was given. Of the 13 animals with kidney specific tolerance, there was a subset of 4 which demonstrated donor alloantigen specific tolerance since they did not reject the C57B1/6 skin. All 4 animals rejected the third party CBA skin, while all 9 Balb/C isografts survived indefinitely. No renal allograft rejection was stimulated by the skin transplants.

EXAMPLE 7

Reversal of Allograft Rejection

To determine whether MB23G2 mAb could reverse acute rejection, seven allografts were performed as described in Example 5, but no immunotherapy was administered until day 4. Untreated allografted kidneys demonstrated rejection at this time. The treated animals received MG23G2, 1.5 mg/kg (50 μg) i.v. daily on days 4, 5 and 6 and no further therapy thereafter. Three animals died of ureteric complications in the MG23G2 treated group—the graft histology did not show rejection at the time of death on days 8, 9 and 25. All the animals had their rejection reversed and the remaining 4 survived >60 days with a normal serum creatinine.

EXAMPLE 8

Effect of MB23G2 on Blood Composition

Figure 3A:
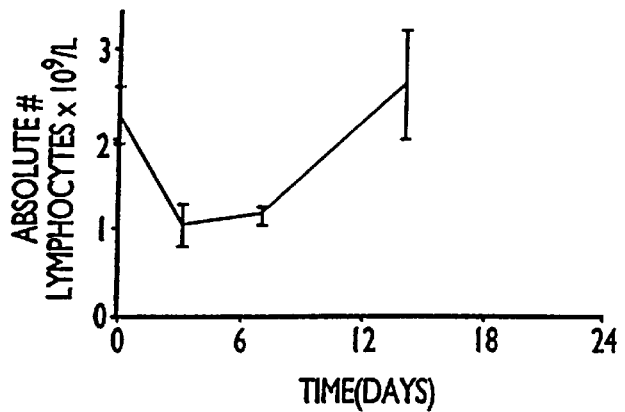
FIGS. 3A, 3B, and 3C shows that MB23G2 induces depletion of circulating lymphocytes and binds to the remaining T and B lymphocytes.
Figure 3B:
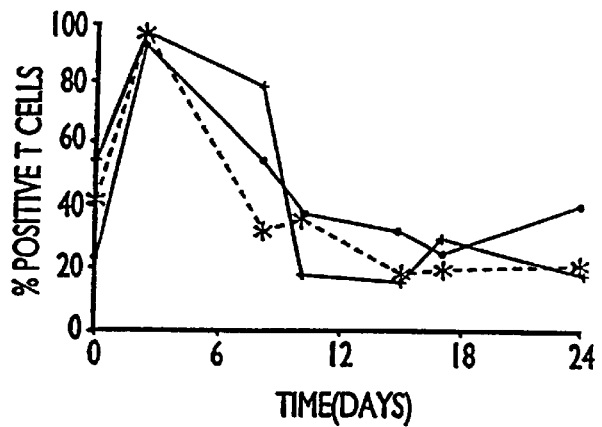
Figure 3C:
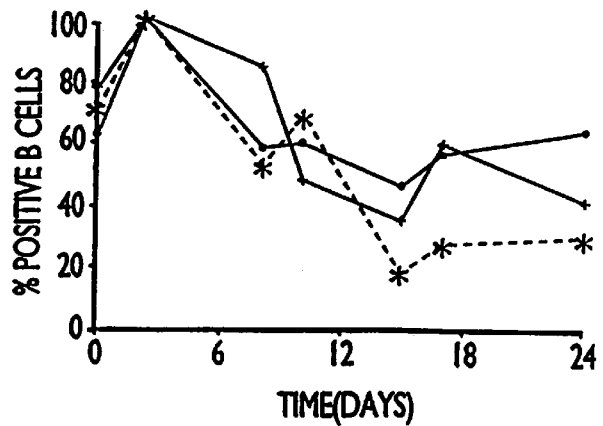

The pharmacologic effects of MB23G2 on the peripheral blood in mice were assessed using multiparameter FACS analysis. Mice were treated with 30 μg of MB23G2 mAb intravenously on two consecutive days. As shown in FIG. 3A, MB23G2 induced a significant depletion of circulating lymphocytes which returned to normal one week after stopping the mAb. MB23G2 bound to almost all the remaining circulating T and B lymphocytes (FIG. 3B and 3C). FACS analysis revealed no excess MB23G2 antibody in the plasma by day 8. FACS analysis of the spleen demonstrated that the administered therapy penetrated the lymphoid tissue 24 hours after the second dose of MB23G2. A FACS inhibition assay did not reveal sensitization of any of the mice to the MB23G2 mAb up to 2 weeks after therapy.

Since CD45 is a protein tyrosine phosphatase, tests were designed to show that induction of allograft tolerance by MB23G2 mAb is related to an alteration in tyrosine phosphorylation of T cell substrates necessary for signal transduction to occur.

EXAMPLE 9

Mechanism of Tolerance Induction by CD45RB Monoclonal Antibody: Increased Tyrosine Phosphorylation of Phospholipase C-γ1 and Decreased Expression of inflammatory Cytokines Murine T cell hybridoma A1.1 cells were stimulated with the CD3 mAb 2C11 in the presence or absence of MB23G2 or MB4B4 mAb. The cells were lysed in Brij 96 and the phosphotyrosine-containing proteins were immunoprecipitated with anti-phosphotyrosine mAb PY72. The immunoprecipitated proteins were extracted and separated on 10% SDS-polyacrylamide gels, transferred electrophoretically to PVDF membranes and submitted to an immunoblotting procedure (See Lazarovits et al., *J. Immunol.*, 153, 3956 (1994)) using the anti-phosphotyrosine mAb 4G10.

Augmentation of tyrosine phosphorylation of a 145 kDa substrate in the presence of the CD45RB MB23G2 mAb was found. The MB4B4 mAb did not alter the tyrosine phosphorylation of this substrate. The identity of this 145 kDa band as PLC-γ1 was confirmed by stripping the 4G10 mAb from the blots and reprobing with monoclonal antibody to phospholipase C-γ1 (PLC-γ1) (Upstate Biotech, Lake Placid, N.Y.). Thus, in the presence of MB23G23, substantially more tyrosine phosphorylated PLC-γ1 could be identified than in its absence, while MB4B4 did not alter the amount of (PLC-γ1) which could be immunoprecipitated. The increased tyrosine phosphorylation of (PLC-γ1) has been noted by Gajewski et al (PROC. NATL. ACAD. SCI. USA, Vol. 91, pp. 38–42 (1994)) to be a property of anergic T cells.

Since gene activation is a consequence of signal transduction in T cells, experiments were performed to investigate whether the MB23G2 mAb could alter the expression of cytokine genes in vivo known to be increased in rejecting allografts. It is generally believed that a so-called TH1 cytokine profile (IL-2, γ-interferon) is associated with rejection, while a TH2 phenotype (IL-4, IL-5, IL-6, IL-10) may be associated with non-responsiveness (see T. R. Mosmann, et al., *J. Immunol.*, 136, 2348 (1986)).

To examine gene expression in mouse renal allografts, steady state levels of specific mRNA transcripts were assessed by Northern Blot analysis using $^{32}$P-labeled cDNA probes. Gene expression in four groups of animals was examined: isografts on postoperative day 7, allografts from untreated animals on postoperative day 7, and allografts from MB23G2-treated animals on postoperative day 7 and day 28. No specific pattern of IL-1, IL-2, IL-4, IL-5, IL-6 or IL-10 was detected. However, there was a selective decrease on day 28 in mRNA transcripts for γ-interferon and tumor necrosis factor α compared to untreated allografts. There was no difference noted on day 7. Interestingly, intercellular adhesion molecule-1 (ICAM) mRNA was also decreased in the MB23G2-treated animals on day 28, with no difference observed on day 7. Thus, the MB23G2 therapy may induce tolerance in part by inhibiting the expression of inflammatory cytokines because of interference with the signal transduction cascade.

In yet other experiments, use of anti-CD45RB antibodies were found to be effective when administered to primates.

EXAMPLE 10

Prevention of Organ Rejection in Primates and Reversal of Organ Rejection

Renal allografts were performed on two Cynomolgous monkeys using a CD45RB monoclonal antibody (which binds to a neuraminidase sensitive epitope), as an immune suppressor and the details are set forth below:

Detailed Experimental Procedures:

1. Animal Care:

The animals were housed in the University of Western Ontario primate facility. They were provided with squeeze cages which allow for drug injections and sample collection without having to anesthetize the animal, thereby reducing stress. They were maintained on standard monkey feed, and other foods for diversity. They were allowed regular exercise in the exercise cage. The animal care followed the standard operating procedures for non-human primates provided by veterinary services.

Animals were typed for blood groups. On arrival, the animals were rested for at least 2 weeks. The animals were anesthetized with atropine and ketamine for physical examination, including inspection for oral B virus, TB testing, and de-wormed with Ivernectin 2828. Animals fasted the night prior to any anesthetics.

2. Kidney Transplantation:

1. Donor procedure:

Two donor animals were injected with ketamine, taken to the OR, intubated and put on insofluorane/nitrous oxide. A three stage surgical prep is used. After a midline incision of the two, the left renal artery, vein and ureter were carefully isolated and divided. Grafts were ex-vivo perfused and stored in 4° C. University of Wisconsin solution. The wounds were closed and the animals returned to the cage to recover from the anesthetic. 200–300 ml of saline were given by continuous i.v. during the surgery. During the surgery, the animals were kept warm using a heating lamp, heated saline and heating pad, etc.

Postoperative care followed Standard Operating Procedures. Briefly, the animals remained on a warm water blanket and under a heating lamp for 24 hours. Buprenorphine was given q6h after surgery for 24 hours. The animals were monitored daily. The well recovered donor animals are used as the recipient in future transplantations. The interval between the two surgeries is at least two weeks.

2. Recipient procedure:

The recipient was anesthetized and prepared preoperatively as described for the donor. After a midline incision, abdominal aorta and inferior vena cava were exposed. End-to-side anastomoses were performed between the donor renal artery and the recipient aorta, as well as between the donor renal vein and the recipient inferior vena cava. The donor ureter was sutured to the recipient's bladder. The right kidney was removed and the wound was closed. 3. Postoperative care:

The post-operative care is the same as described for the donor. Animals were monitored continually post-operatively for at least 24 hours, more if necessary. They were monitored closely (i.e., several times per day) until feeding and grooming normally. Thereafter, they were monitored at least daily when they received their monoclonal antibody.

Animals were given 4 mg of anti-CD45RB 6G3 mAb 4 i.v. daily for 7 days. The outcome of kidney grafts was measured by percutaneous biopsy weekly and blood creatinine levels twice per week. For these procedures animals were anesthetized with ketamine. Criteria for early euthanasia would include lethargy, lack of grooming or feeding, significant weight loss (>20%) and renal failure (elevated creatinine levels).

As discussed above, the recipient animals received 4 mg (1 mg/kg) of anti-CD45RB 6G3 mAb post operatively for 7 days. There were no side effects associated with such infusions. Both animals survived normally until day 16 when each experienced an acute rejection crises. The first animal was euthanized 2 days later on day 18. The second animal was re-treated with 4 mg/kg (16 mg) of anti-CD45RB 6G3 mAb. This therapy was given daily i.v. for four days. Remarkably the rejection crises completely reversed as the animal was observed to resume normal activities and creatine levels were observed to decrease from a "crises" level of 738 μmol/L to 366 μmol/L. The animal remained well until day 36 when another rejection crises developed. The animal was than euthanized. Histology of the allograft revealed that there was profound endothelitis on post-operative day 15 just before additional therapy was administered leading to reversal. A biopsy of the allograft of this animal was performed on post-operative day 23 revealing the endothellitis had cleared.

It is known that control animals will die by day 10 if therapy is not administered in this type of model. (Lazarovits et al., Kidney Inter., 25, 344 (1984)).

The data suggests two conclusions:

[1] Because both monkeys lived past the known date of controls, it is shown the therapy of the invention exhibits significant graft-survival in a primate.

[2] Even more dramatic is the observation that one can reverse acute rejection with anti-CD45RB monoclonal antibodies.

EXAMPLE 11

Additional Monkey Experiments

Two additional Cynomolgus monkeys (#3 and #4) have received renal allografts and have been treated with the CD45RB monoclonal antibody 6G3 as the sole form of immunosuppression. Blood grouping was performed to control for ABO compatibility and major histocompatibility complex profiles were obtained using PCR based DNA typing to confirm that allogeneic renal transplants were being performed.

On day zero, a nephrectomy was performed in the recipient animal and the renal allograft was performed. On day seven the second native kidney was removed and from that point on the animal relied on its transplanted kidney. Animals which do not receive immunosuppression or which receive ineffective immunosuppression will reject at a mean of ten days +/−two days (Lazarovits et al., Kidney Intern., 25, 344 (1984)).

Monkey #3

This animal was treated with 6G3 antibody 2 mg/kg/day (8 mg)×7 days and then 6 more doses given on Monday, Wednesday and Friday for each of the next two weeks was to be given. Thus, 8 mg of 6G3 antibody was planned to be given over three weeks. The animal developed rejection on day 14 and was euthanized.

Monkey #4

This animal received the same therapy as monkey #3. That is 8 mg of 6G3 antibody was given intravenously for 13 doses over three weeks. This animal has done remarkably well and continues to be alive beyond 70 days. No rejection has been diagnosed.

Figure 4:
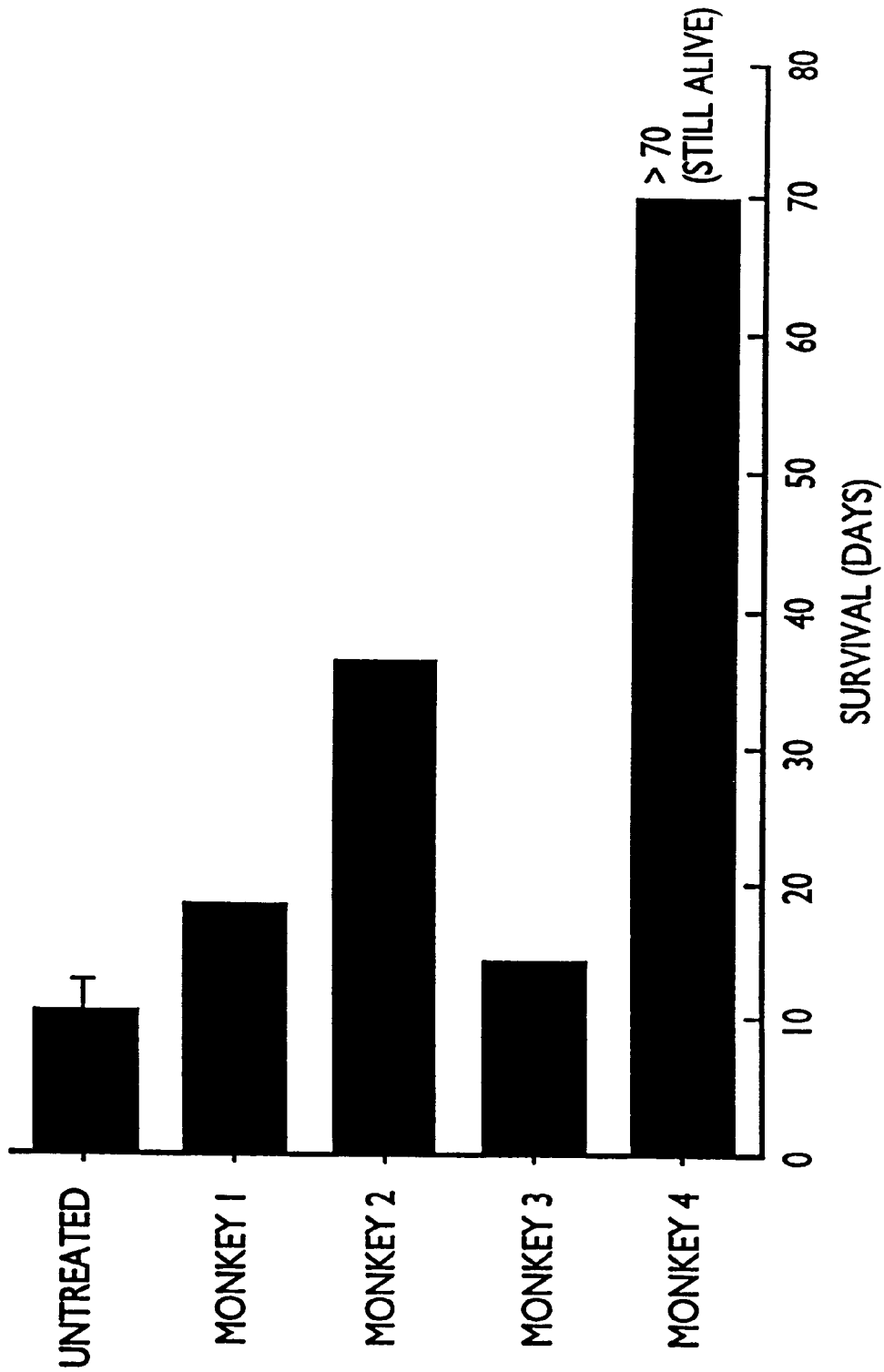
FIG. 4 shows the survival of Cynomolgus monkeys treated with anti-CD45RB mAb 6G3, after receipt of allografts.

Thus, animals #3 and #4 treated with 6G3 have had significantly prolonged allograft survival which is illustrated in FIG. 4. Monkey #2 of Example 8 is of particular interest because the antibody successfully reversed acute rejection which was predicted by the mouse kidney transplant experiments. Additional experiments are underway to try to determine the cause for relatively early graft failure in monkeys 1 and 3, although both of these animals also had significantly prolonged allograft survival.

EXAMPLE 12

In Vivo Prevention of the Rejection of Heart Transplants in Mice

Heterotopic heart transplants from C57B1/6 mice into BALB/C donors were performed essentially as described in R. L. Kirkman et al (1985) Transplantation 40: 719–722. Seven of the mice received 30 μg iv of rat anti-mouse CD45RB mAb MB23G2 on days 0 and 1 following heart transplantation. Four other mice received 30 μg i.v. on days 0 and 1 and 100 μg ip of rat anti-mouse CD45RB mAb MB23G2 daily on days 2 to 11 following heart transplantation. Fourteen control mice received no antibody. Survival of the heterotopic graft was determined by whether the heart was beating and rejection was confirmed by histological analysis.

All of the control mice had rejected their hearts by day 14 post-operation, with a mean survival time of 9 days. Mean survival time of the hearts in the group receiving antibody for two days only was 20 days and mean survival time of the hearts in the group receiving antibody for 11 days was 34 days. Table V summarizes the results from this experiment.

TABLE V

| MOUSE CARDIAC ALLOGRAFTS | | | |
|---|---|---|---|
| Groups | Number | Survival (days) | Mean |
| Untreated | 14 | 8, 8, 9, 9, 9, 9, 9, 9, 9, 10, 11, 11, 11, 14 | 9 |
| CD45RB mAb 30 μg D0, D1 | 7 | 16, 16, 17, 22, 24, 23, 24 | 20 |

TABLE V-continued

MOUSE CARDIAC ALLOGRAFTS

| Groups | Number | Survival (days) | Mean |
|---|---|---|---|
| CD45RB mAb 30 μg IV D0, D1 AND 100 μg ip × 9 days | 4 | 15, 30, 38, 38 | 34 |

Additional evidence of the utility of anti-CD45RB was demonstrated in the following studies.

EXAMPLE 13

In Vivo Pevention of the Rejection of Pancreatic Islet Allograft Transplants in Mice Pancreatic islet allografts were transplanted under the kidney capsule from CBA/J donors into streptozotocin-treated BALB/C recipients essentially as described in M. C. Fabian et al., *Transplantation*, 56, 1137 (1993). Five control mice received no antibody while eleven mice received 30 μg i.v. of rat anti-mouse CD45RB mAb MB23G2 on days 0 to 1 post-operation. Rejection was defined as onset of glycosuria. All islet allografts from control mice had been rejected by day 24 with a mean rejection time of 17 days. Antibody-treated mice showed a mean rejection time of 34 days with two mice having no signs of rejection at day 50 when the experiment was stopped.

Table VI summarizes the result from this experiment.

TABLE VI

MOUSE PANCREATIC ISLET ALLOGRAFTS

| Groups | Number | Survival (days) | Mean |
|---|---|---|---|
| Untreated | 5 | 12, 12, 15, 24, 20 | 17 |
| CD45RB mAb 0 μg iv D0, D1 | 11 | 23, 32, 20, 30, 30 >50, >50, 21, 23, 47, 50 | 34 |

EXAMPLE 14

Induction of Xenograft Tolerance in Rat to Mouse Transplant Models

To assess whether anti-CD45RB monoclonal antibody could prevent xenogeneic renal graft rejection, orthotopic kidney xenografts were performed in BALB/c mice with Lewis rats as donors. Five groups of recipients were studied: no treatment (Controls), cyclosporin (CsA) treatment (5 mg/kg S.C. daily), splenectomy (Spl), cyclophosphamide (CyP) treatment (20 mg/kg on POD 0, 2, 4 & 7), MB23G2 mAb treatment (100 μg daily×11 days, I.P.), and combined treatment with MB23G2 mAb (100 μg×11 days) and CyP (20 mg/kg I.V. on POD 0, 2, 4 & 7). As shown below in Table VII, animals treated with MB23G2 mAb and CyP had a significantly longer median survival time than animals treated with mAb alone or CyP alone, demonstrating that CD45RB mAb and CyP have a synergistic effect on prolonging renal xenografts in the mouse.

TABLE VII

RAT-TO-MOUSE KIDNEY XENOGRAFTS

| Group | n | Treatment | Survival (days) | Median Survival (Days) |
|---|---|---|---|---|
| Control | 6 | None | 6(4), 7, 16 | 6 |
| CsA | 3 | Cyclosporin | 4, 6, 8 | 6 |
| Spl | 5 | Splenectomy | 4, 5, 6, 7, 11 | 6 |
| CyP | 8 | Cyclophosphamide | 10, 18, 23, 24, 28, 49, 58, >100 | 26 |
| mAb | 6 | MB23G2 | 4, 6, 8, 8, 11, 13 | 8 |
| mAb + CyP | 9 | CyP + MB23G2 | 9, 11, 23, 24, 70, 76, >100(3) | 70* |

*P <0.01, the mAb group vs the control group.

The ultimate goal for clinical xenotransplantation is to induce xenograft tolerance, thereby eliminating the continuous use of toxic, high-dose immunosuppression. It was recently demonstrated in a hamster heart to mouse xenograft model that the combination of pulse therapy with CyP and continuous CsA treatment induced prolonged graft survival. See Hasan et al., *Transplantation*, 54, 408 (1992). However, when the cyclosporin therapy was stopped, the xenografts were rejected within a short period of time, i.e., the median survival time was less than three weeks. Thus, therapy with CyP and CsA was unable to induce xenograft tolerance.

In contrast, as shown in Table VII above, xenografts in animals treated with CD45RB mAb and CyP continued to survive several months after cessation of immunosuppressive therapy. Moreover, the long term surviving kidney xenografts treated with mAb and CyP had a normal renal function and a normal pathology at sacrifice on POD 100. These results demonstrate that treatment with CD45RB mAb and CyP can induce functional xenograft tolerance in a rat-to-mouse model. This therapy may be applicable in the prevention of transplant rejection in man.

EXAMPLE 15

In Vivo Treatment of NOD Mice to Inhibit the Onset of Diabetes

Five female NOD mice were treated with 30 μg iv of rat anti-mouse CD45RB mAb MB23G2 on days 28, 29 and 30 after birth. Five control mice received no antibody treatment. By week 27 all control mice were dead as a result of diabetes. Of the antibody-treated mice 2 died of diabetes while the other 3 remained alive and well until week 35 at which point they were killed and their pancreas examined histologically. There was no sign of insulitis in any of the three surviving animals.

Table VIII summarizes the results from this experiment.

TABLE VIII

ONSET OF DIABETES IN NOD MICE

| Groups | Number | Survival Without Diabetes |
|---|---|---|
| Untreated | 5 | 0 (all dead by 27 weeks) |
| CD45RB mAb 30 μg iv days 28, 29, 30 | 5 | 3 > 35 weeks |

Additional experiments have been conducted since this preliminary experiment was conducted. The therapy in these experiments comprised administering 100 ug of MG23G2 two times per week from 2–35 weeks, at which time all remaining mice were euthanized. The results are shown in Table IX below:

TABLE IX

NOD MOUSE SURVIVAL (WEEKS)

| THERAPY | SURVIVAL WEEKS | INSULITIS SCORE* (MEAN) |
|---|---|---|
| MB23G2 (N = 9) | 35(6), 20(2), 13 | 0.99 |
| CONTROL (N = 12) | 34 (2), 30 (2), 28, 23, 18, 16, 15, 14, 13, 12 | 1.81 |

*Insulitis score obtained from 6 additional animals in each group at 15 weeks.

As seen from the data a significantly greater number of animals survived indefinitely, i.e., until the end of the 35 week experiment compared to the controls. The improvement induced by MB23G2 is evident not only in animal survival but also in blood sugar where all of the animals who survived to 35 weeks in the treated group had no evidence of hyperglycemia. The beneficial effect of MB23G2 was also confirmed by the insulitis score which is a careful histologic assessment of the pancreas. The difference between 1.81 and 0.99 is both biologically and statistically meaningful.

EXAMPLE 16

Prevention of Skin Graft Rejection

Four groups of A-strain mice (white) will receive skin grafts from C57BL/10-strain mice (black): groups I and II will receive prior treatment with rat anti-mouse CD45RB mAb and groups III and IV will receive no prior treatment with rat anti-mouse CD45RB mAb. Following the skin graft operation, groups I and III are treated with anti-mouse CD45RB mAb on varying days, while groups II and IV receive no further antibody treatment. The effectiveness of the antibody treatment in preventing rejection of the skin graft is determined by comparing the length of time the black skin graft survives on the white recipient mice in the four groups.

EXAMPLE 17

Localized Graft-Versus-Host (GvH) Reaction

In vivo efficacy of the compounds will be demonstrated in a suitable animal model, as described, e.g., in Ford et al., Transplantation, 10, 258 (1970). Spleen cells ($1 \times 10^7$) from 6 week old female mice are injected subcutaneously on day 0 into the left hind-paw of mice of a different strain weighing about 100 g. Animals are treated for 4 consecutive days and the popliteal lymph nodes are removed and weighed on day 7. The difference in weight between the two lymph nodes is taken as the parameter for evaluating the reaction.

EXAMPLE 18

Freund's Adjuvant Arthritis

Efficacy against experimentally induced arthritis can be demonstrated using the procedure described, e.g., in Winter & Nuss, ARTHRITIS & RHEUMATISM 9 (1966) 394; Billingham Davies, HANDBOOK OF EXPERIMENTAL PHARMACOL. (Vane & Ferreira Eds, Springer-Verlag, Berlin) 50/II (1979) 108–144. Mice (male or female, 150 g body weight) are injected, i.e., at the base of the tail or in the hind paw, with 0.1 ml of mineral oil containing 0.6 mg of lyophilized heat-killed Mycobacterium smegmatis. In the developing arthritis model, treatment is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper. $ED_{50}$ is the oral dose in mg/kg which reduces the swelling (primary or secondary) to half of that of the controls.

EXAMPLE 19

In Vivo Treatment of NZB Mice to Inhibit Onset of Lupus-Like Autoimmune Disease

Mice of the New Zealand black-strain (NZB) die with widespread and diverse symptoms of hemolytic anemia, glomerulonephritis, and vasculitis, all very reminiscent of human systemic lupus erythematosus (SLE). The effectiveness of the present invention in treating SLE is evaluated in this mouse model by treating newborn NZB mice with rat anti-mouse CD45RB mAb MB23G2 at varying times after birth and then analyzing treated and untreated mice for the onset of autoimmune disease, particularly for glomerulonephritis, which is also a prominent feature of human SLE.

EXAMPLE 20

In-Vitro Evaluation of the Imunomodulatory Activity of CD45 Reagents

The ability of anti-human CD45 antibodies to suppress human T-cell activation was evaluated in vitro by the following method.

Mononuclear cells were isolated from the peripheral blood of volunteers by Ficoll-Hypaque density gradient centrifugation. The cells were stimulated in RPMI1640 with 10% FCS with OKT3 or a non-reactive control antibody for periods of 1–4 days. The percentages of CD3, CD4 and CD8 cells positive for CD69 as a marker of early and CD25 as a marker of late activation were determined by FACScan analysis. Poppema et al., Leukemia and Lymphoma, 20, 217 (1996). The effect of CD45 and CD45R antibodies was measured by adding these reagents as singles or as cocktails. Western blots of the cell lysates were stained with anti-phosphorylated tyrosine antibody 4G10 to investigate the potential role of dephosphorylation as a result of the tyrosine phosphatase activity of CD45. June et al., J. Immunol., 144, 1591(1990).

Figure 5:
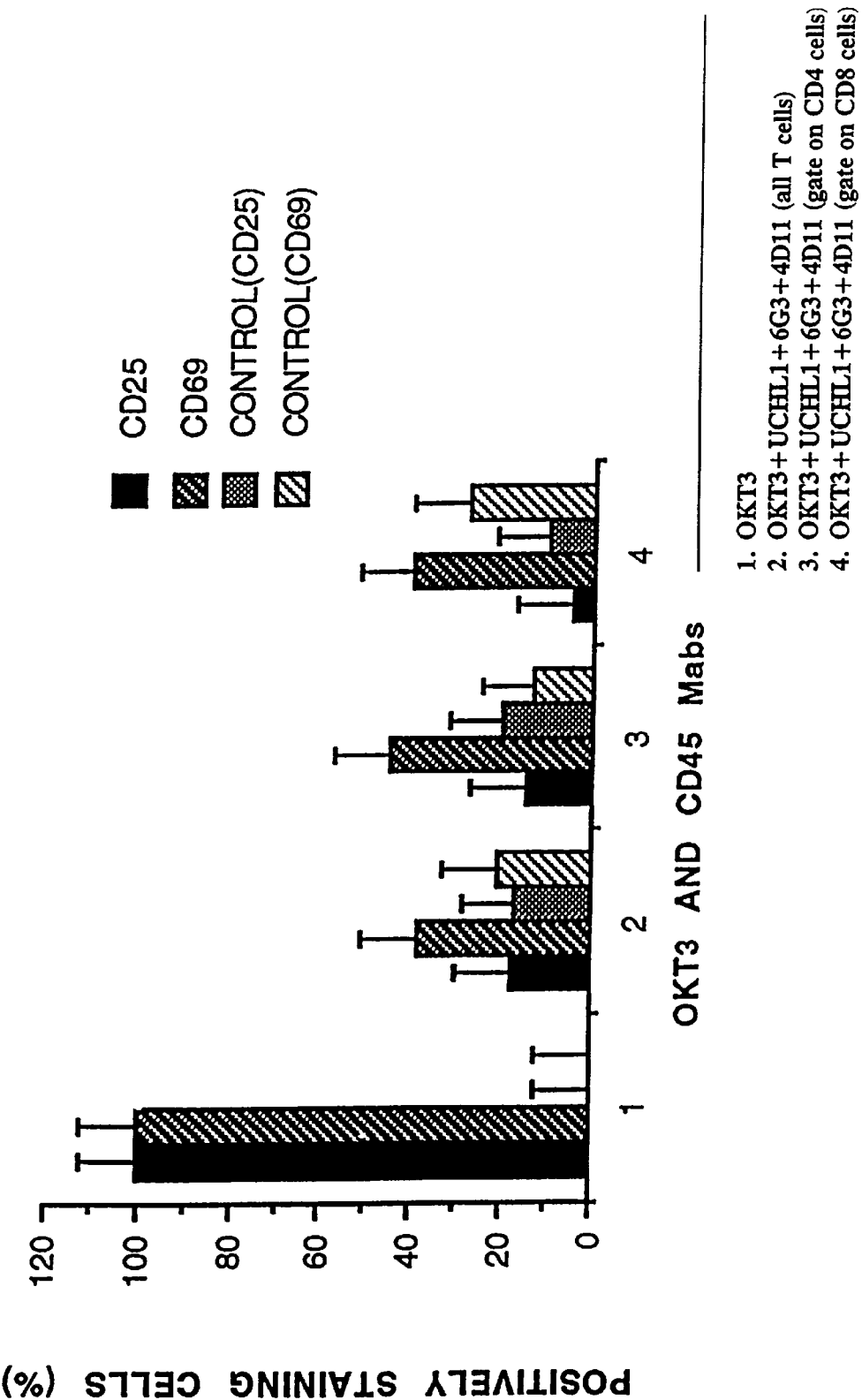
FIG. 5 shows the results of co-incubation of the CD45(R) antibodies with OKT3 stimulated peripheral blood mononuclear cells.

As shown in Table XIII below, OKT3 caused CD25 expression on approximately 70% of the T cells on day 4, whereas exposure to a non-reactive control antibody resulted in approximately 10% CD25 expression. None of the CD45 (R) antibodies alone led to T-cell activation. The results of co-incubation of the CD45(R) antibodies with OKT3 stimulated peripheral blood mononuclear cells are summarized in FIG. 5. The four CD45RA reagents tested had no effect or resulted in slight stimulation. Of four CD45RB reagents tested 2 (6B6, 6G3) gave significant inhibition whereas the other two (MT3, PD7) only had minimal effects. Of three CD45RO reagents tested one gave significant inhibition (UCHL1) whereas the other two (A6, OPD4) showed much less inhibition. Of four CD45 reagents tested one (4C9) had no effect, two (4D 11, 2G1) gave inhibition and one (4F9) resulted in stimulation clearly above the effect of OKT3 alone.

TABLE X

CORRELATION OF ACTIVATION AND TYROSINE PHOSPHORYLATION

| Antibodies | % CD25 | Tyrosine Phosphorylation 110 kDa Band |
|---|---|---|
| OKT3 plus control ab | 70% | yes |
| OKT3 plus 6B6 (RB) | 45% | no |
| OKT3 plus 6G3 (RB) | 45% | no |
| OKT3 plus MT3 (RB) | 65% | yes (slightly weaker) |
| OKT3 plus PD7 (RB) | 70% | yes |

Figure 6:
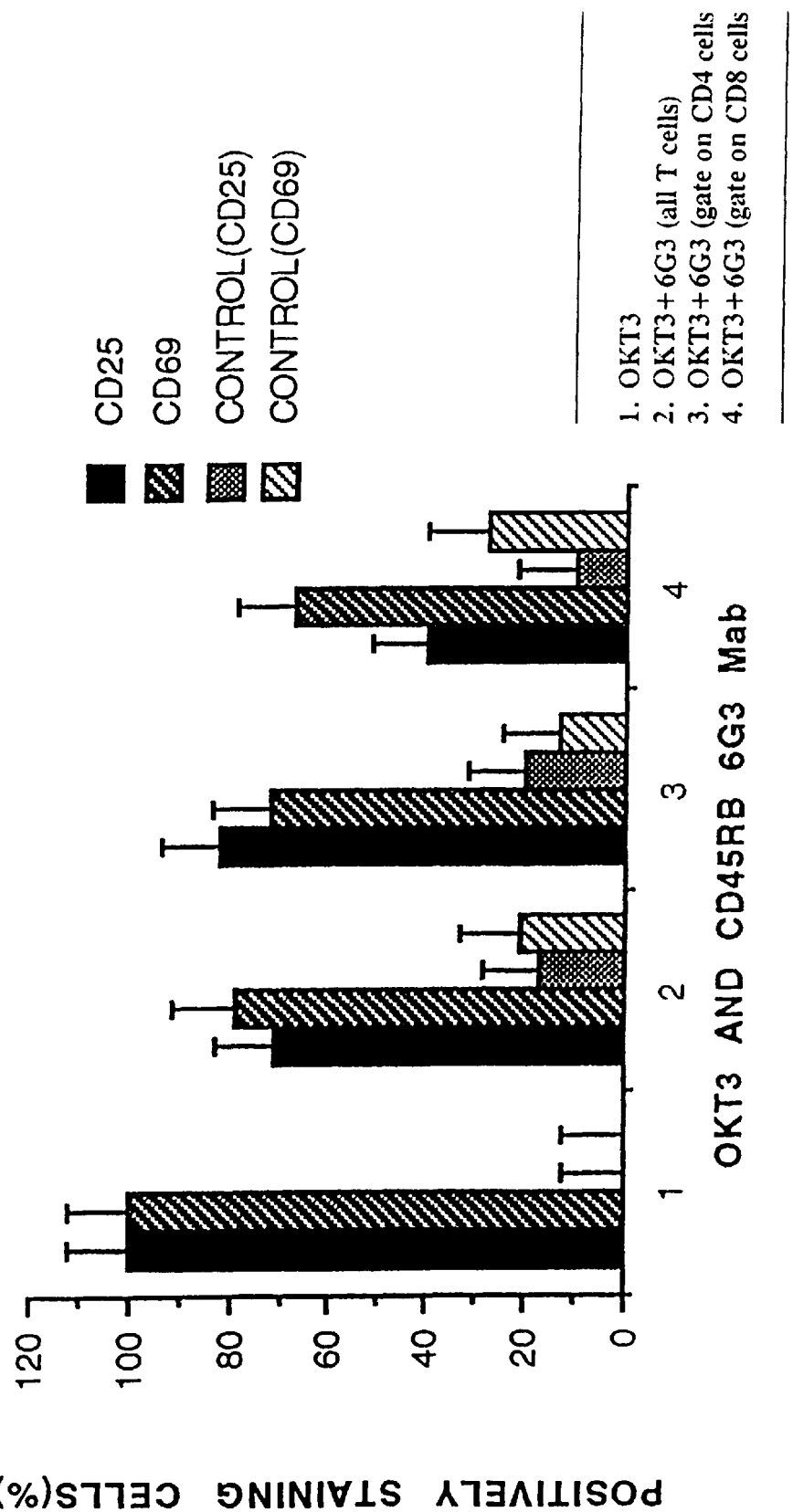
FIG. 6 shows that anti-CD45RB reagent 663 has a greater inhibiting effect on CD8 cells than on CD4 cells.
Figure 7:
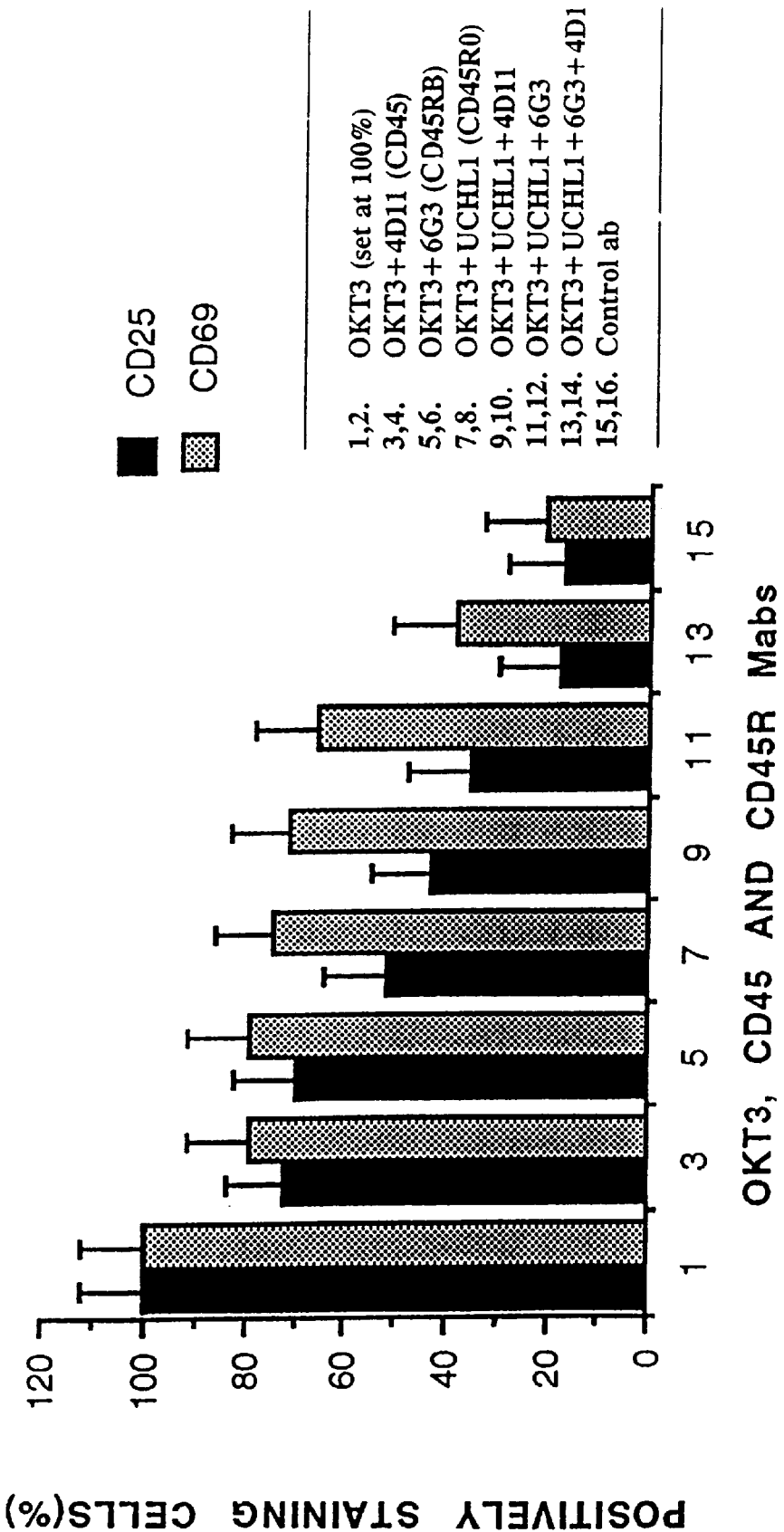
FIG. 7 shows the inhibitory effect of CD45, CD45RB and CD45RO antibodies on OKT3 induced CD25 expression.

The expression of CD25 and CD69 was also analyzed after gating for CD4+ or CD8+ T cells. The results indicate that anti-CD45RB reagent 6G3 has a much more pronounced inhibitory effect on CD8 cells than on CD4 cells. See FIG. 6. Combinations of reagents were also tested and as is shown in FIG. 7, clear synergy of a CD45, CD45RB and CD45RO mixture was found, which reduced the level of CD25 expression to that not significantly different from the non-stimulated controls.

The results of this study demonstrate that CD45(R) specific antibodies can modulate CD3 mediated T-cell activation in vitro. The results of combinations of antibodies indicate that different mechanisms may contribute to the measured effect.

The finding that some, but not other, anti-CD45RB antibodies inhibit T-cell activation is in accordance with the finding that one CD45RB specific antibody does enhance renal allograft survival in a mouse model while another does not. See Example 5. The predominant inhibitory effect of the CD45RB antibodies on CD8 cells is in agreement with the finding that the major immunophenotypic finding in the successfully treated mice is a reduction of the number of CD8 cells in the allograft.

In conclusion, analysis of CD25 expression of in vitro CD3 stimulated peripheral blood T cells demonstrates the immunomodulatory activity of anti-CD45(R) antibodies. A mixture of anti-human CD45(R) antibodies is a powerful inhibitor of T-cell activation in vitro and may well be suitable for the prevention and reversion of allograft rejection.

All patents, patent applications and publications are incorporated herein by reference, as though fully set forth. Thus, it is apparent that there has been provided, in accordance with the present invention, methods and products which will substantially benefit those with autoimmune diseases and those receiving organ transplants. While the invention has been described in conjunction with specific embodiments thereof, it is evident that many modifications and variations will be apparent to those skilled in the art. Accordingly, it is intended to include all such alternatives, modifications and variations set forth within the spirit and scope of the appended claims.

What is claimed is:

1. A method for treating or preventing cell, tissue or organ transplant rejection in a mammalian recipient, comprising administering to said recipient at least one antibody that specifically binds to a CD45RB epitope of the CD45RB isotype of the leukocyte antigen, and at least one antibody that specifically binds to a CD45RO epitope of the CD45RO isotype of the leukocyte antigen in an amount effective to inhibit a T-cell mediated immune response in the recipient.

2. The method of claim 1, wherein said cell, tissue or organ transplant is allogeneic to the recipient.

3. The method of claim 1, wherein said cell, tissue or organ transplant is xenogeneic to the recipient.

4. The method of claim 1 wherein the antibodies bind to a neuraminidase sensitive epitope on said antigen.

5. The method of claim 1 wherein the antibodies are administered prior to transplantation of the cell, tissue or organ.

6. The method of claims 1 or 5 wherein the antibodies are administered following transplantation of the cell tissue or organ.

7. The method of claims 1 or 5 wherein the antibodies are administered concurrently with transplantation of the cell, tissue or organ.

8. The method of claim 1 wherein the CD45RO antibody is an anti-CD45RO monoclonal antibody or an antigen-binding fragment thereof.

9. The method of claims 1, 2, 3 or 4, further comprising administering at least one anti-inflammatory or immunosuppressive drug.

10. The method of claim 9, wherein said anti-inflammatory or immunosuppressive drug is cyclosporin, cyclophosamide, FK-506, rapamycin, corticosteroids, mycophenolate mofetil, leflunomide, Anti-Lymphocyte Globulin, deoxyspergualin or OKT-3.

11. The method of claims 1, 2, 3 or 4, further comprising administering an amount of lymphocytes of said recipient, that have been previously exposed ex vivo to said antibody.

12. The method of claim 1 which further comprises administration of an amount of an antibody, a synthetic analogue or fragment thereof that specifically binds to a CD45RA epitope of the CD45RA isotype leukocyte antigen, and an antibody, a synthetic analogue or fragment thereof that specifically binds to the CD45RC epitope of the CD45RC isotype leukocyte antigen or mixtures thereof.

13. The method of claims 1, 2, 3 or 4 wherein the tissue is pancreatic islets.

14. The method of claims 1, 2, 3 or 4 wherein the organ is a kidney.

15. The method of claims 1, 2, 3 or 4 wherein the organ is a heart.

16. The method of claims 1, 2, 3 or 4 wherein the tissue is vascular tissue.

17. The method of claims 1, 2, 3 or 4 wherein the cells are hematopoietic cells.

18. The method of claims 1, 2, 3 or 4 wherein the organ is liver.

19. The method of claims 1, 2, 3 or 4 wherein the recipient is a human.

* * * * *

UNITED STATES PATENT AND TRADEMARK OFFICE
CERTIFICATE OF CORRECTION

PATENT NO. : 6,106,834
DATED : August 22, 2000
INVENTOR(S) : Lazarovits et al.

It is certified that error appears in the above-identified patent and that said Letters Patent is hereby corrected as shown below:

In column 1, line 59, delete "$R^A$" and insert --$R_A$-- therefor.
In column 5, line 24, delete "pharmnaceutical" and insert --pharmaceutical-- therefor.
In column 13, line 23, delete "$5x10_{-5}$" and insert --$5x10^{-5}$-- therefor.
In column 13, line 65, delete "$2x10_5$" and insert --$2x10^5$-- therefor.
In column 17, line 35, delete "inflammatory" and insert --Inflammatory-- therefor.
In column 19, line 11, after "closed.", insert new paragraph.

Signed and Sealed this

First Day of May, 2001

Attest:

NICHOLAS P. GODICI

Attesting Officer                Acting Director of the United States Patent and Trademark Office